(12) United States Patent
deLong et al.

(10) Patent No.: US 6,451,859 B1
(45) Date of Patent: Sep. 17, 2002

(54) $C_{16}$ UNSATURATED FP-SELECTIVE PROSTAGLANDINS ANALOGS

(75) Inventors: Mitchell Anthony deLong, West Chester; David Lindsey Soper, Mason; John August Wos; Biswanath De, both of Cincinnati, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/914,531

(22) PCT Filed: Feb. 29, 2000

(86) PCT No.: PCT/US00/05299

§ 371 (c)(1), (2), (4) Date: Aug. 29, 2001

(87) PCT Pub. No.: WO00/51979

PCT Pub. Date: Sep. 8, 2000

Related U.S. Application Data

(60) Provisional application No. 60/122,929, filed on Mar. 5, 1999.

(51) Int. Cl.⁷ ............... C07C 405/00; A61K 31/5575
(52) U.S. Cl. ............ 514/570; 514/530; 560/60; 562/440; 562/455; 562/463; 562/470; 562/622; 564/99
(58) Field of Search ............ 560/60; 562/440, 562/463, 455, 470, 622; 564/94; 514/530, 570

(56) References Cited

FOREIGN PATENT DOCUMENTS

WO 2000051979 * 9/2000 .............. 514/530

* cited by examiner

*Primary Examiner*—Robert Gerstl
(74) *Attorney, Agent, or Firm*—David V. Upite; James C. Kellerman

(57) ABSTRACT

Compounds having a structure according to the following formula:

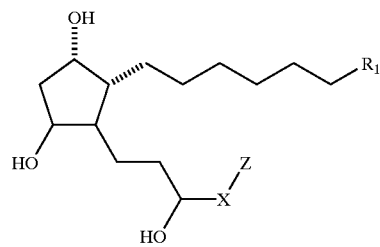

are effective in treating disorders such as bone disorders and glaucoma in a subject in need thereof.

20 Claims, No Drawings

$C_{16}$ UNSATURATED FP-SELECTIVE PROSTAGLANDINS ANALOGS

This application is a 371 of PCT/US00/05299, filed Feb. 29, 2000, which claims benefit of Provisional application Ser. No. 60/122,929, filed Mar. 5, 1999.

TECHNICAL FIELD

The subject invention relates to certain novel analogs of the naturally occurring prostaglandins. Specifically, the subject invention relates to novel Prostaglandin F analogs. The subject invention further relates to methods of using said novel Prostaglandin F analogs. Preferred uses include methods of treating bone disorders and glaucoma.

BACKGROUND OF THE INVENTION

Naturally occurring prostaglandins (PGA, PGB. PGE, PGF, and PGI) are C-20 unsaturated fatty acids. $PGF_{2\alpha}$, the naturally occurring Prostaglandin F in humans, is characterized by hydroxyl groups at the $C_9$ and $C_{11}$ positions on the alicyclic ring, a cis-double bond between $C_5$ and $C_6$, and a trans-double bond between $C_{13}$ and $C_{14}$. Thus $PGF_{2\alpha}$, has the following formula:

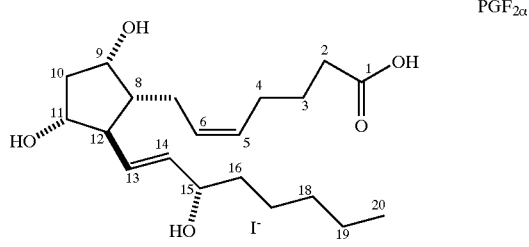

$PGF_{2\alpha}$

Analogs of naturally occurring Prostaglandin F have been disclosed in the art. For example, see U.S. Pat. No. 4,024, 179 issued to Bindra and Johnson on May 17, 1977; German Patent No. DT-002,460,990 issued to Beck, Lerch, Seeger, and Teufel published on July 1, 1976; U.S. Pat. No. 4,128, 720 issued to Hayashi, Kori, and Miyake on Dec. 5, 1978; U.S. Pat. No. 4,011,262 issued to Hess, Johnson, Bindra, and Schaaf on Mar. 8,. 1977; U.S. Pat. No. 3,776,938 issued to Bergstrom and Sjovall on Dec. 4, 1973; P. W. Collins and S. W. Djuric, "Synthesis of Therapeutically Useful Prostaglandin and Prostacyclin Analogs", *Chem. Rev.* Vol. 93 (1993), pp. 1533–1564; G. L. Bundy and F. H. Lincoln, "Synthesis of 17-Phenyl-18,19,20-Trinorprostaglandins: I. The $PG_1$ Series", *Prostaglandins*, Vol. 9 No. 1 (1975), pp. 1–4; W. Bartman, G. Beck, U. Lerch, H. Teufel, and B. Scholkens, "Luteolytic Prostaglandins: Synthesis and Biological Activity", *Prostaglandins*, Vol. 17 No. 2 (1979), pp. 301–311; C. liljebris, G. Selen, B. Resul, J. Sternschantz, and U. Hacksell, "Derivatives of 17-Phenyl-18,19,20-trinorprostaglandin $F_2\alpha$ isopropyl Ester: Potential Antiglaucoma Agents", *Journal of Medicinal Chemistry*, Vol. 38 No. 2 (1995), pp. 289–304.

Naturally occurring prostaglandins are known to possess a wide range of pharmacological properties. For example, prostaglandins have been shown to: relax smooth muscle, which results in vasodilatation and bronchodilatation, to inhibit gastric acid secretion, to inhibit platelet aggregation, to reduce intraocular pressure, and to induce labor. Although naturally occurring prostaglandins are characterized by their activity against a particular prostaglandin receptor, they generally are not specific for any one prostaglandin receptor. Therefore, naturally-occurring prostaglandins are known to cause side effects such as inflammation, as well as surface irritation when administered systemically. It is generally believed that the rapid metabolism of the naturally occurring prostaglandins following their release in the body limits the effects of the prostaglandin to a local area. This effectively prevents the prostaglandin from stimulating prostaglandin receptors throughout the body and causing the effects seen with the systemic administration of naturally occurring prostaglandins.

Prostaglandins, especially prostaglandins of the E series (PGE), are known to be potent stimulators of bone resorption. $PGF_{2\alpha}$ has also been shown to be a stimulator of bone resorption but not as potent as $PGE_2$. Also, it has been demonstrated the $PGF_{2\alpha}$ has little effect on bone formation as compared to $PGE_2$. It has been suggested that some of the effects of $PGF_{2\alpha}$ on bone resorption, formation and cell replication may be mediated by an increase in endogenous $PGE_2$ production.

In view of both the wide range of pharmacological properties of naturally occurring prostaglandins and of the side effects seen with the systemic administration of these naturally occurring prostaglandins, attempts have been made to prepare analogs to the naturally occurring prostaglandins that are selective for a specific receptor or receptors. A number of such analogs have been disclosed in the art. Though a variety of prostaglandin analogs have been disclosed, there is a continuing need for potent, selective prostaglandin analogs for the treatment of a variety diseases and conditions.

SUMMARY OF THE INVENTION

The invention provides novel PGF analogs. In particular, the present invention relates to compounds having a structure according to the following formula:

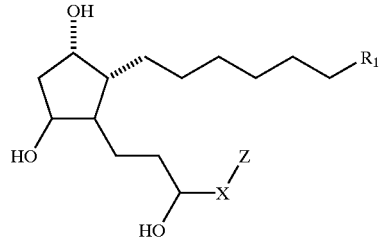

wherein $R_1$, X, and Z are defined below.

This invention also includes optical isomers, diastereomers and enantiomers of the formula above, and pharmaceutically-acceptable salts, biohydrolyzable amides, esters, and imides thereof.

The compounds of the present invention are useful for the treatment of a variety of diseases and conditions, such as bone disorders and glaucoma. Accordingly, the invention further provides pharmaceutical compositions comprising these compounds. The invention still further provides methods of treatment for bone disorders and glaucoma using theses compounds or the compositions containing them.

DETAILED DESCRIPTION OF THE INVENTION

Terms and Definitions

"Alkyl" is a saturated or unsaturated hydrocarbon chain having 1 to 18 carbon atoms, preferably 1 to 12, more preferably I to 6, more preferably still 1 to 4 carbon atoms. Alkyl chains may be straight or branched. Preferred branched alkyl have one or two branches, preferably one branch. Preferred alkyl are saturated. Unsaturated alkyl have one or more double bonds and/or one or more triple bonds. Preferred unsaturated alkyl have one or two double bonds or one triple bond, more preferably one double bond. Alkyl chains may be unsubstituted or substituted with from 1 to 4 substituents. Preferred substituted alkyl are mono-, di-, or trisubstituted. The substituents may be lower alkyl, halo, hydroxy, aryloxy (e.g., phenoxy), acyloxy (e.g., acetoxy), carboxy, monocyclic aromatic ring (e.g., phenyl), monocyclic heteroaromatic ring, monocyclic carbocyclic aliphatic ring, monocyclic heterocyclic aliphatic ring, and amino.

"Lower alkyl" is an alkyl chain comprised of 1 to 6, preferably 1 to 3 carbon atoms.

"Aromatic ring" is an aromatic hydrocarbon ring. Aromatic rings are monocyclic or fused bicyclic ring systems. Monocyclic aromatic rings contain from about 5 to about 10 carbon atoms, preferably from 5 to 7 carbon atoms, and most preferably from 5 to 6 carbon atoms in the ring. Bicyclic aromatic rings contain from 8 to 12 carbon atoms, preferably 9 or 10 carbon atoms in the ring system. Bicyclic aromatic rings include ring systems wherein one ring in the system is aromatic. Preferred bicyclic aromatic rings are ring systems wherein both rings in the system are aromatic. Aromatic rings may be unsubstituted or substituted with from 1 to 4 substituents on the ring. The substituents may be halo, cyano, alkyl, heteroalkyl, haloalkyl, phenyl, phenoxy or any combination thereof. Preferred substituents include halo and haloalkyl. Preferred aromatic rings include naphthyl and phenyl. The most preferred aromatic ring is phenyl.

"Carbocyclic aliphatic ring" is a saturated or unsaturated. hydrocarbon ring. Carbocyclic aliphatic rings are not aromatic. Carbocyclic aliphatic rings are monocyclic. Carbocyclic aliphatic rings contain from about 4 to about 10 carbon atoms, preferably from 4 to 7 carbon atoms, and most preferably from 5 to 6 carbon atoms in the ring. Carbocyclic aliphatic rings may be unsubstituted or substituted with from 1 to 4 substituents on the ring. The substituents may be halo, cyano, alkyl, heteroalkyl, haloalkyl, phenyl, phenoxy or any combination thereof. Preferred substituents include halo and haloalkyl. Preferred carbocyclic aliphatic rings include cyclopentyl, cyclohexyl, cyclohexenyl, cycloheptyl, and cyclooctyl. More preferred carbocyclic aliphatic rings include cyclohexyl, cycloheptyl, and cyclooctyl.

"Halo" is fluoro, chloro, bromo or iodo. Preferred halo are fluoro, chloro and bromo; more preferred are chioro and fluoro, especially fluoro.

"Haloalkyl" is a straight, branched, or cyclic hydrocarbon substituted with one or more halo substituents; Preferred haloalkyl are $C_1$–$C_{12}$; more preferred are $C_1$–$C_6$; more preferred still are $C_1$–$C_3$. Preferred halo substituents are fluoro and chloro. The most preferred haloalkyl is trifluoromethyl.

"Heteroalkyl" is a saturated or unsaturated chain containing carbon and at least one heteroatom, wherein no two heteroatoms are adjacent. Heteroalkyl chains contain from 1 to 18 member atoms (carbon and heteroatoms) in the chain, preferably 1 to 12, more preferably 1 to 6, more preferably still 1 to 4. Heteroalkyl chains may be straight or branched. Preferred branched heteroalkyl have one or two branches, preferably one branch. Preferred heteroalkyl are saturated. Unsaturated heteroalkyl have one or more double bonds and/or one or more triple bonds. Preferred unsaturated heteroalkyl have one or two double bonds or one triple bond, more preferably one double bond. Heteroalkyl chains may be unsubstituted or substituted with from 1 to 4 substituents. Preferred substituted heteroalkyl are mono-, di-, or trisubstituted. The substituents may be lower alkyl, halo, hydroxy, aryloxy (e.g., phenoxy), acyloxy (e.g., acetoxy), carboxy, monocyclic aromatic ring (e.g., phenyl), monocyclic heteroaromatic ring, monocyclic carbocyclic aliphatic ring, monocyclic heterocyclic aliphatic ring, and amino.

"Lower heteroalkyl" is a heteroalkyl chain comprised of 1 to 6, preferably 1 to 3 member atoms.

"Heteroaromatic ring" is an aromatic ring containing carbon and from 1 to about 4 heteroatoms in the ring. Heteroaromatic rings are monocyclic or fused bicyclic ring systems. Monocyclic heteroaromatic rings contain from about 5 to about 10 member atoms (carbon and heteroatoms), preferably from 5 to 7, and most preferably from 5 to 6 in the ring. Bicyclic heteroaromatic rings include ring systems wherein only one ring in the system is aromatic. Preferred bicyclic heteroaromatic rings are ring systems wherein both rings in the system are aromatic. Bicyclic heteroaromatic rings contain from 8 to 12 member atoms, preferably 9 or 10 in the ring. Heteroaromatic rings may be unsubstituted or substituted with from 1 to 4 substituents on the ring. The substituents may be halo, cyano, alkyl, heteroalkyl, haloalkyl, phenyl, phenoxy or any combination thereof. Preferred substituents include halo, haloalkyl, and phenyl. Preferred monocyclic heteroaromatic rings include thienyl, thiazolo, purinyl, pyrimidyl, pyridyl, and furanyl. More preferred monocyclic heteroaromatic rings include thienyl, furanyl, and pyridyl. The most preferred monocyclic heteroaromatic ring is thienyl. Preferred bicyclic heteroaromatic rings include benzo[β]thiazolyl, benzo[β]thiophenyl, quinolinyl, quinoxalinyl, benzo[β]furanyl, benzimidizolyl, benzoxazolyl, indolyl, and anthranilyl. More preferred bicyclic heteroaromatic rings include benzo[β]thiazolyl, benzo[β]thiophenyl, and benzoxazolyl.

"Heteroatom" is a nitrogen, sulfur, or oxygen atom. Groups containing more than one heteroatom may contain different heteroatoms.

"Heterocyclic aliphatic ring" is a saturated or unsaturated ring containing carbon and from 1 to about 4 heteroatoms in the ring, wherein no two heteroatoms are adjacent in the ring and no carbon in the ring that has a heteroatom attached to it also has a hydroxyl, amino, or thiol radical attached to it. Heterocyclic aliphatic rings are not aromatic. Heterocyclic aliphatic rings are monocyclic. Heterocyclic aliphatic rings contain from about 4 to about 10 member atoms (carbon and heteroatoms), preferably from 4 to 7 member atoms, and most preferably from 5 to 6 member atoms in the ring. Heterocyclic aliphatic rings may be unsubstituted or substituted with from 1 to 4 substituents on the ring. The substituents may be halo, cyano, alkyl, heteroalkyl, haloalkyl, phenyl, phenoxy or any combination thereof. Preferred substituents include halo and haloalkyl. Preferred heterocyclic aliphatic rings include piperzyl, morpholinyl, tetrahydrofuranyl, tetrahydropyranyl and piperdyl.

"Phenyl" is a monocyclic aromatic ring which may or may not be substituted with from about 1 to about 4 substituents. The substituents may be fused but not bridged and may be substituted at the ortho, meta or para position on the phenyl ring, or any combination thereof. The substituents may be halo, acyl, cyano, alkyl, heteroalkyl, haloalkyl, phenyl, phenoxy or any combination thereof. Preferred substituents on the phenyl ring include halo and haloalkyl. The most preferred substituent is halo. The preferred substitution pattern on the phenyl ring is ortho or meta. The most preferred substitution pattern on the phenyl ring is meta.

Compounds

The subject invention involves compounds having the following structure:

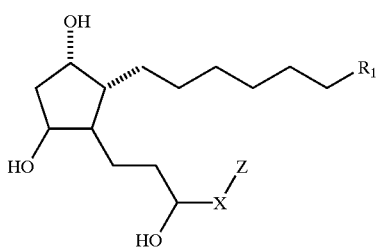

Formula A

In the above structure, $R_1$ is $CO_2H$, $C(O)NHOH$, $CO_2R_2$, $CH_2OH$, $S(O)_2R_2$, $C(O)NHR_2$, $C(O)NHS(O)_2R_2$, or tetrazole; wherein $R_2$ is alkyl, heteroalkyl, carbocyclic aliphatic ring, heterocyclic aliphatic ring, monocyclic aromatic ring, or monocyclic heteroaromatic ring and $R_3$ is lower alkyl, lower heteroalkyl, or haloalkyl. Preferred $R_2$ is methyl, ethyl, and isopropyl. Preferred $R_1$ is $CO_2H$, $C(O)NHOH$, $CO_2R_2$, $C(O)NHS(O)_2R_2$, and tetrazole. Most preferred $R_1$ is $CO_2H$ and $CO_2R_2$.

In the above structure, X is CH=C=CH, CH=CH, CH=N, C(O), or C(O)Y; wherein Y is O, S, or NH. Preferred X is CH=C=CH, CH=N, C(O), and C(O)Y. X is not part of an aromatic or heteroaromatic ring system.

In the above structure, Z is an aromatic ring or a heteroaromatic ring provided that when Z is a heteroaromatic ring Z is attached via a Carbon member atom. Preferred Z is monocyclic aromatic ring. More preferred Z is furanyl, thienyl, and phenyl.

The invention also includes optical isomers, diastereomers and enantiomers of the above structure. Thus, at all stereocenters where stereochemistry is not defined ($C_{11}$, $C_{12}$, and $C_{15}$), both epimers are envisioned. Preferred stereochemistry at all such stereocenters of the compounds of the invention mimic that of naturally occurring $PGF_{2\alpha}$.

It has been discovered that the novel PGF analogs of the subject invention are useful for treating bone disorders, especially those that require a significant increase in bone mass, bone volume, or bone strength. Surprisingly, the compounds of the subject invention have been found to provide the following advantages over known bone disorder therapies: (1) An increase trabecular number through formation of new trabeculae; (2) An increase in bone mass and bone volume while maintaining a more normal bone turnover rate; and/or (3) An increase in bone formation at the endosteal surface without increasing cortical porosity.

In order to determine and assess pharmacological activity, testing of the subject compounds in animals is carried out using various assays known to those skilled in the art. For example, the bone activity of the subject compounds can be conveniently demonstrated using an assay designed to test the ability of the subject compounds to increase bone volume, mass, or density. An example of such assays is the ovariectomized rat assay.

In the ovariectomized rat assay, six-month old rats are ovariectomized, aged 2 months, and then dosed once a day subcutaneously with a test compound. Upon completion of the study, bone mass and/or density can be measured by dual energy x-ray absorptometry (DXA) or peripheral quantitative computed tomography (pQCT), or micro computed tomography (mCT). Alternatively, static and dynamic histomorphometry can be used to measure the increase in bone volume or formation.

Pharmacological activity for glaucoma can be demonstrated using assays designed to test the ability of the subject compounds to decrease intraocular pressure. Examples of such assays are described in the following reference, incorporated herein: C. liljebris, G. Selen, B. Resul, J. Sternschantz, and U. Hacksell, "Derivatives of 17-Phenyl-18,19,20-trinorprostaglandin $F_2\alpha$ Isopropyl Ester: Potential Antiglaucoma Agents", *Journal of Medicinal Chemistry*, Vol. 38 No. 2 (1995), pp. 289–304.

Compounds useful in the subject invention can be made using conventional organic syntheses. Particularly preferred syntheses are carried out using the following general reaction schemes, Schemes I, II, and Ill. Scheme I describes a general reaction scheme for making compounds of the invention wherein X is CH=CH (Formula I) or CH=C=CH (Formula II). Scheme II describes a general reaction scheme for making compounds of the invention wherein X is C(O) (Formula III) or C(O)Y (Formula IV). Scheme III describes a general reaction scheme for making compounds of the invention wherein X is CH=N (Formula V).

Scheme 1

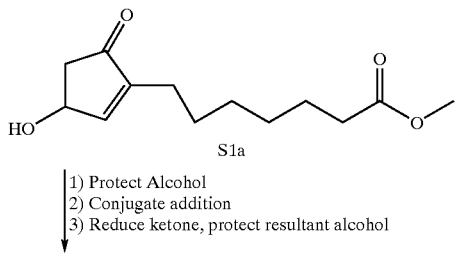

S1a

1) Protect Alcohol
2) Conjugate addition
3) Reduce ketone, protect resultant alcohol

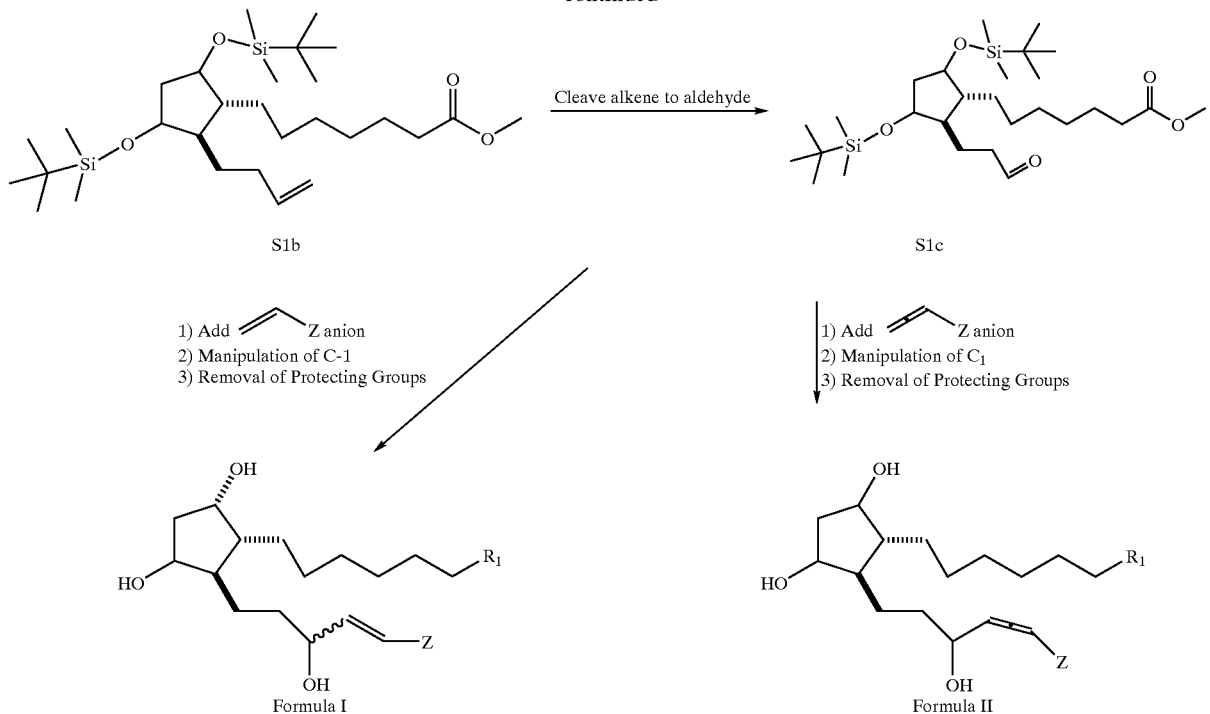

In Scheme 1, $R_1$ and Z are as defined above. The methyl 7[3-(R)-hydroxy-5-oxo-1-cyclopent-1-y] heptanoate (S1a) depicted as starting material for Scheme 1 is commercially available (such as from Sumitomo Chemical or Cayman Chemical).

In the above Scheme 1, Methyl 7-[3-(R)hydroxy-5-oxo-1-cyclopent-1-yl] heptanoate (S1a) is reacted with a silylating agent and base in a solvent that will allow the silylation to proceed. Preferred silylating agents include tert-butyldimethylsilyl chloride and tert-butyidimethylsilyl trifluoromethanesulphonate. The most preferred silylating agent is tert-butyldimethylsilyl trifluoromethanesulphonate. Preferred bases include triethylamine, trimethylamine, and 2,6-lutidine. More preferred bases include triethylamine and 2,6-lutidine. The most preferred base is 2,6-lutidine. Preferred solvents include halocarbon solvents with dichlorbmethane being the most preferred solvent. The reaction is allowed to proceed at a temperature preferably between −100° C. and 100° C., more preferably between −80° C. and 80° C., and most preferably between −70° C. and 23° C.

The resulting silylated compound is isolated by methods known to one of ordinary skill in the art. Such methods include, but are not limited to, extraction, solvent evaporation, distillation, and crystallization. Preferably, the silyl ether is purified after isolation by distillation under vacuum.

The silylated compound is then reacted with the cuprate generated via Grignard formation of the appropriate alkenyl bromide as disclosed, for example, in the following references: H. O. House et. al., "The Chemistry of Carbanions: A Convenient Precursor for the Generation of Lithium Organocuprates", *J. Org. Chem.* Vol. 40 (1975) pp. 1460–69; and P. Knochel et. al., "Zinc and Copper Carbenoids as Efficient and Selective a'/d' Multicoupling Reagents", *J. Amer. Chem. Soc.* Vol. 111 (1989) p. 6474–76. Preferred alkenyl bromides include 4-bromo-1-butene, 4-bromo-1-butyne, 4-bromo-2-methyl-1-butene, and 4-bromo-2-ethyl-1-butene. The most preferred alkenyl bromide is 4-bromo-1-butene. Preferred solvents include ethereal solvents, of which diethyl ether and tetrahydrofuran are preferred. The most preferred solvent is tetrahydrofuran. The Grignard reagent is allowed to form at a temperature between 100° C. and 23° C., more preferably between 85° C. and 30° C., and most preferably between 75° C. and 65° C. The reaction time is preferably between 1 hour and 6 hours, with a more preferred reaction time being between 2 hours and 5 hours, and the most preferred reaction time being between 3 hours and 4 hours.

Once the Grignard reagent is formed, the cuprate is generated from the alkenyl magnesium species. The temperature range for cuprate formation is between —100° C. and 0° C. The preferred temperature range is between −80° C. and −20° C. The more preferred temperature range is between −75° C. and −50° C. The preferred reaction time is between 30 minutes and 6 hours. The more preferred reaction time is between 45 minutes and 3 hours. The most preferred reaction time is between 1 hours and 1.5 hours.

The alkene thus formed is isolated by methods known to one of ordinary skill in the art. Such methods include, but are not limited to, extraction, solvent evaporation, distillation, and crystallization. Preferably, the alkene is purified by flash chromatography on silica gel (Merck, 230–400 mesh) using 10% EtOAc/hexanes as the eluent. The alkene is then reacted with a hydride reducing agent and a polar, protic solvent to give the C-9 alcohol. Preferred reducing agents include lithium aluminum hydride, sodium borohydride, and L-selectride. More preferred reducing agents include sodium borohydride, and L-selectride. The most preferred reducing agent is sodium borohydride. Preferred solvents include methanol, ethanol, and butanol. The most preferred solvent is methanol. The reduction is carried out at a temperature between −100° C. and 23° C. The preferred temperature range is between −60° C. and 0° C. The most preferred temperature range is between −45° C. and −20° C.

The resulting alcohol is isolated by methods known to one of ordinary skill in the art. Such methods include, but are not limited to, extraction, solvent evaporation, distillation, and crystallization. Preferably, the alcohol is purified by flash chromatography on silica gel (Merck, 230–400 mesh) using 20% EtOAc/hexanes as the eluent.

The resultant alcohol can be protected as described previously herein. Preferred silylating agents in this case also include tert-butyidimethylsilyl chloride and tert-butydimethylsilyl trifluoromethanesulfonate. The most preferred silylating agent is tert-butyidimethylsilyl trifluoromethanesulfonate. Preferred bases include triethylamine, trimethylamine, and 2,6-lutidine. More preferred bases include triethylamine and 2,6-lutidine. The most preferred base is 2,6-lutidine. Preferred solvents include halocarbon solvents with dichloromethane being the most preferred solvent. The reaction is allowed to proceed at a temperature preferably between −100° C. and 100° C., more preferably between −80° C. and 80° C., and most preferably between −70° C. and 23° C.

The resulting silylated compound, S1b is isolated by methods known to one of ordinary skill in the art. Such methods include, but are not limited to, extraction, solvent evaporation, distillation, and crystallization. Preferably, the silyl ether is purified after isolation by distillation under vacuum, giving compound S1b.

The protected alcohol is then treated with a form of osmium and sodium periodate in a solvent where they are both soluble. Preferred forms of osmium include osmium tetraoxide and potassium osmate. Preferred solvent systems include 1:1 mixtures of acetic acid and water and 1:1:2 mixtures of water, acetic acid and THF. The result of this treatment is the aldehyde, S1c.

The compound S1c is isolated by methods known to one of ordinary skill in the art. Such methods include, but are not limited to, extraction, solvent evaporation, distillation, and crystallization. Preferably, S1c is purified by flash chromatography on silica gel (Merck, 230–400 mesh) using 20% EtOAc/hexanes as the eluent.

The key intermediate aidehyde depicted as S1c can be reacted with a variety of unsaturated alkenyl anion nucleophiles to provide the C-9 and C-11-protected 13,14-dihydroprostaglandin $F_{1\alpha}$ derivatives.

The resulting compounds can be isolated, but are generally deprotected using techniques known to one of ordinary skill in the art, and optionally, manipulated at C-1 to provide the desired acid derivative at $R_1$. For example, the condensation of a methyl ester with an amine or a hydroxylamine provides an amide or a hydroxamic acid compound, respectively. After any such manipulation at C-1, the compounds are isolated as the final 13,14dihydro-15-substituted-15-pentanor prostaglandin $F_{1\alpha}$ derivative, Formula I. Compounds depicted by Formula I are exemplified in Examples 1–12,18, and 20.

Compounds depicted by Formula II can be made directly from intermediate S1c in a manner similar to that for compounds depicted by Formula I substituting the appropriate allene anion. With allene nucleophiles, the reaction is carried out preferably at between −80° C. and 0° C., more preferably between −80° C. and −20° C., and most preferably between −80° C. and −40° C. Preferred bases for the reaction include n-butyl lithium, s-butyl lithium, and t-butyl lithium. The most preferred base is n-butyl lithium. Preferred solvents for the reaction are ether solvents. Preferred solvents include diethyl ether, and tetrahydrofuran. The most preferred solvent is tetrahydrofuran. With heterocyclic nucleophiles, preferred solvents include ethereal solvents. More preferred ethereal solvents include diethyl ether, dibutyl ether and tetrahydrofuran. The most preferred ethereal solvent is tetrahydrofuran. After isolation, similar C-1 manipulations and/or deprotection of the functional groups ensues using techniques known to one of ordinary skill in the art. Compounds depicted by Formula II are exemplified in Examples 13–17 and 19.

Scheme II

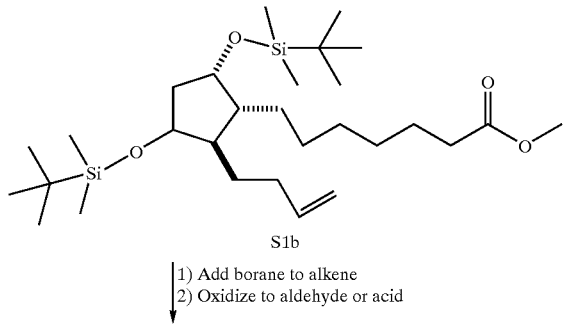

S1b

1) Add borane to alkene
2) Oxidize to aldehyde or acid

-continued

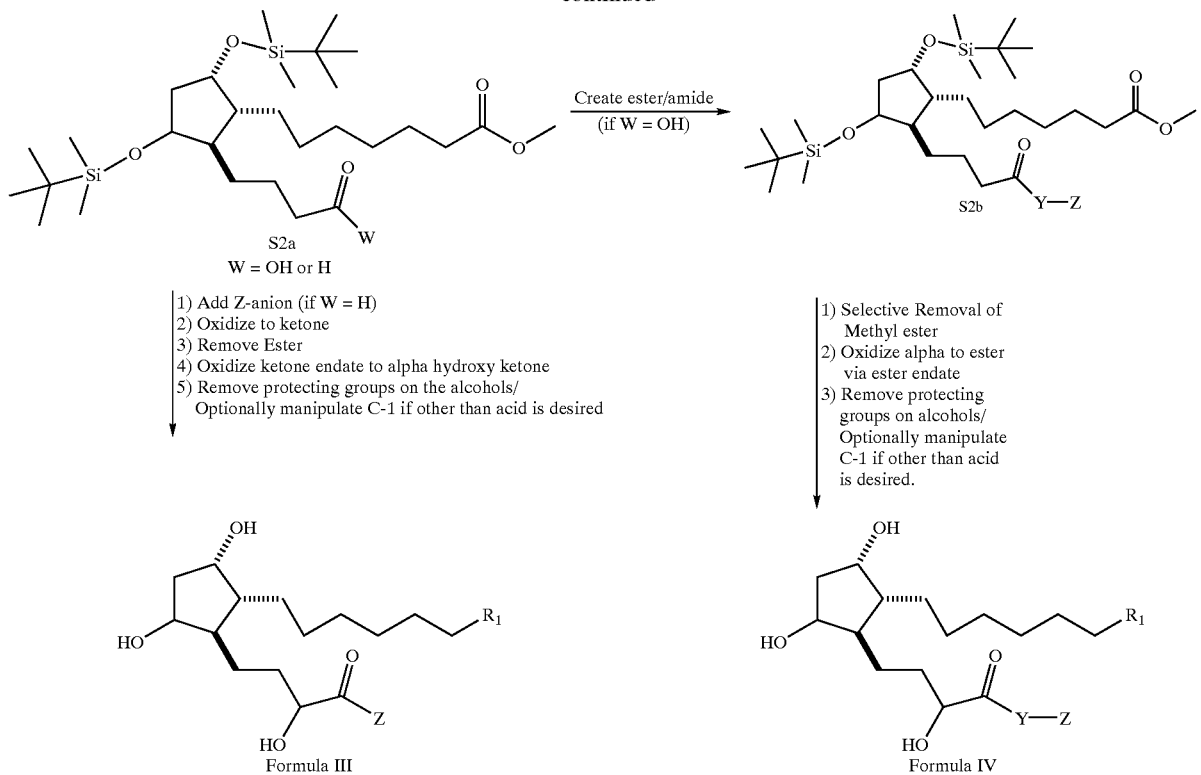

In Scheme 2, $R_1$, Y, and Z are as defined above. The protected alcohol S1b (from Scheme 1) is treated with a hydroborating reagent in an ethereal solvent, followed by oxidative removal of the boron reagent with a suitable oxidant to give a compound of the type S2a. Preferred hydroborating reagents include monochloroborane-dimethylsulfide, diborane, borane-tetrahydrofuran and borane-dimethylsulfide. The most preferred hydroborating reagent is borane-dimethylsulfide. Preferred ethereal solvents include THF and diethyl ether. The most preferred solvent is THF. The reaction is carried out from about 1 to about 24 hours at a temperature of from about −20° C. to about +30° C. The preferred temperature range is from about 0° C. to about +20° C. The hydroborated product of this reaction may then be oxidatively removed to the alcohol using alkaline hydrogen peroxide (See. Boranes in *Organic Chemistry*, H. C. Brown, Cornell University Press, Ithaca, N.Y. 1972, pp. 321–325), which may then be oxidized to either the aldehyde (W=H) or to the acid (W=OH) using methods known to one of ordinary skill in the art. Alternatively, the hydroborated product may be directly oxidized to the aldehyde or acid by treatment with chromic acid or a Cr(VI) salt. Such salts include pyridinium chlorochromate (PCC) and dichlorochromate. See Brown, H. C.; Kulkarni, Rao, and Patil, Tetrahedron, 1986, 45515. The preferred method is treatment of the hydroborated product with PCC in dichlororhethane at room temperature. The result of these manipulations is a compound of the type S2a.

The compound S2a is isolaited by methods known to one of ordinary skill in the art. Such methods include, but are not limited to, extraction, solvent evaporation, distillation, and crystallization. Preferably, S2a is purified by flash chromatography on silica gel (Merck, 230–400 mesh) using 20% EtOAc/hexanes as the eluent with 0.1% acetic acid added if W=OH.

The key intermediate aldehyde depicted as S2a can be reacted with a variety unsaturated carbon nucleophiles to provide the C-9 and C-11-protected 13,14-dihydro-16-tetranor prostaglandin $F_{1\alpha}$ derivatives of Formula III.

With aromatic and heteroaromatic nucleophiles, the reaction is carried out preferably at between −80° C. and 0° C., more preferably between −80° C. and −20° C., and most preferably between −80° C. and −40° C. Preferred bases for the reaction include n-butyl lithium, s-butyl lithium, lithium diisopropylamide, and t-butyl lithium. The most preferred base is n-butyl lithium. Preferred solvents for the reaction are ether solvents. Preferred solvents include diethyl ether, and tetrahydrofuran. The most preferred solvent is tetrahydrofuran. With heterocyclic nucleophiles, preferred solvents include ethereal solvents. More preferred ethereal solvents include diethyl ether, dibutyl ether and tetrahydrofuran. The most preferred ethereal solvent is tetrahydrofuran.

The resulting alcohol can be isolated, but is generally oxidized as a crude isolate. The oxidation of benzylic alcohols to benzylic ketones is well known in the art. The preferred reagents to effect this reaction include KMnO4, MnO2, chromic acid, Jones' reagent, Collins' reagent, and PCC. The most preferred method is oxidation at room temperature in dichloromethane with PCC for about 4 hours. The ketones are isolated by column chromatography using 20% hexanes/ethyl acetate as solvent. The ester is then removed using standard conditions. See Greene and Wuts, *Protecting Groups in Organic Synthesis*, Wiley Interscience, NY pp.224–276. The free acid is then treated with 2.1 equivalents of a strong nitrogen base to effect deprotonation both of the acid and adjacent to the benzylic ketone. Such bases include LDA. This enolate is reacted with a peroxidizing agent which has the effect of oxidizing the compound to deliver the alpha-hydroxy ketone. Such reagents include meta-chloroperoxybenzoic acid, dimethyl dioxirane, Davis'. reagent and peracetic acid. The crude product may be isolated or the remaining protecting groups may be removed. At this point manipulation of the acid at C-1 may take place. For example, re-esterifying, making the amide, the hydroxamic acid or the sulfonamide using methods known to one of ordinary skill in the art may be performed to yield compounds according to Formula III. Compounds depicted by Formula III are exemplified in Examples 21–30.

Compounds depicted by Formula IV can be made from intermediate S2b. In this case, condensation of the free acid is readily achieved with a variety of alcohols and amines, either by the use of coupling agents such as DCC, or by activating the acid with, for example, oxalyl chloride. Following this is the selective removal of the methyl esters as described in Greene and Wuts, *Protecting Groups in Organic Synthesis*, Wiley Interscience, NY pp.224–276, and the oxidation of the ester enolates using the same technique described above for the ketone intermediates. Similarly, as described above, the remaining protecting groups are removed and the desired manipulation of C-1 is effected, yielding compounds of Formula IV. Compounds depicted by Formula IV are exemplified in Examples 31–40.

In Scheme 3, $R_1$ and Z are as defined above. The alkene S1b (from Scheme 1) is treated with an osmium salt and with an optional catalyst reoxidant, preferably N-methyl morpholine N-oxide (NMO), to give the diol. This diol is isolated by extraction and purified by silica gel chromatography. The diol is then oxidized selectively to the alpha hydroxy aidehyde. This may be accomplished in several ways. For example, a selective oxidant such as DMSO-oxalyl chloride may be used. Alternatively, the primary alcohol may be selectively protected, then the secondary alcohol protected, then the protection on the primary alcohol may then be removed and the alcohol oxidized as described above in Scheme II. However, the preferred method is the addition of a o-bromo-benzyl bromide protecting group, which can be removed with concomitant oxidation by tributyl tin hydride and like reagents. This technique yields compounds of the type S3a, wherein P=H. From this step follows the condensation of the aldehyde with an amine to form an imine of the type S3b. Appropriate removal of protecting groups and manipulation of C-1 as stated above in Schemes I and II yields compounds according the Formula V. Compounds depicted by Formula V are exemplified in Examples 41–48.

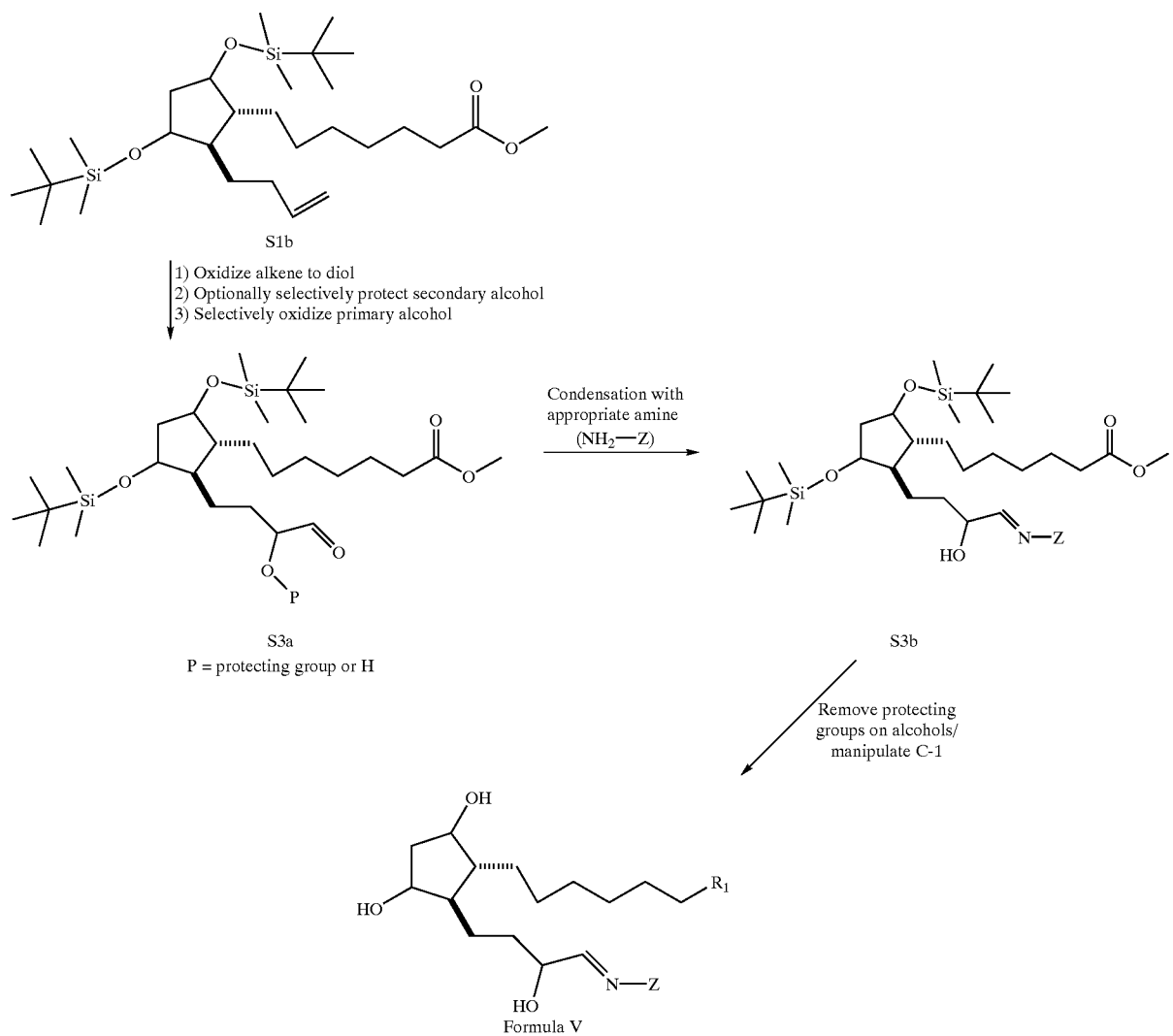

The following non-limiting examples illustrate the compounds, compositions, and uses of the present invention.

EXAMPLES

Compounds are analyzed using $^1H$ and $^{13}C$ NMR, Elemental analysis, mass spectra, high resolution mass spectra and/or IR spectra as appropriate.

Typically, inert solvents are used, preferably in dried form. For example, tetrahydrofuran (THF) is distilled from sodium and benzophenone, diisopropylamine is distilled from calcium hydride and all other solvents are purchased as the appropriate grade. Chromatography is performed on silica gel (70–230 mesh; Aldrich) or (230–400 mesh; Merck) as appropriate. Thin layer chromatography analysis is performed on glass mounted silica gel plates (200–300 mesh; J. T. Baker) and visualized using uv light, 5% phosphomolybdic acid in EtOH, or ammonium molybdate/cerric sulfate in 10% aqueous $H_2SO_4$.

Example 1

Preparation of 13,14-Dihydro-16-17-Z-didehyro-17-(2-fluorophenyl) prostaglandin $F_{1\alpha}$

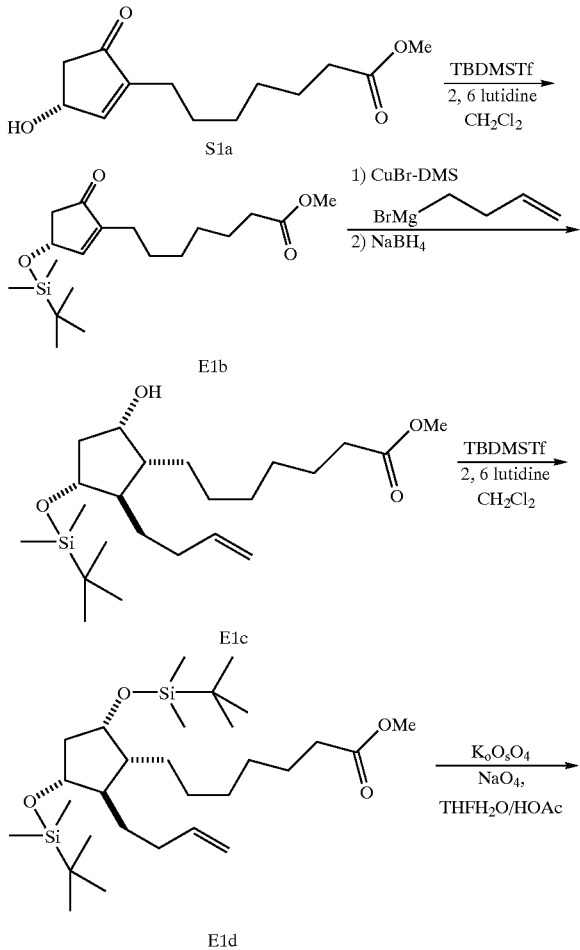

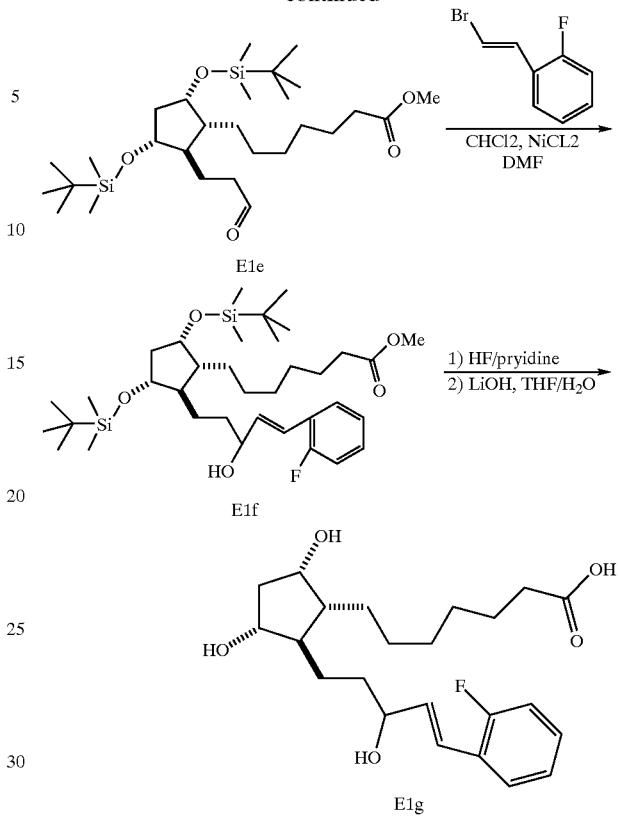

a. Methyl 7-(2-oxo-4-(1,1,2,2-tetramethyl-1-silapropoxy) cyclopent-1-enyl) heptanoate (E1b): To a solution of Methyl-7-[3-(R)-hydroxy-5-oxo-1-cyclopenten-1-yl] heptanoate S1a (1 equiv.) in $CH_2Cl_2$ at −78° C. is added 2,6 Lutidine (1.3 equiv.) dropwise over 15 minutes. The solution is kept at −78° C. TBDMS Triflate (1.2 equiv.) in $CH_2Cl_2$ is added dropwise over 15 minutes. The reaction is warmed gradually to room temperature and stirred at room temperature for 15 hours. Aqueous 10% HCl is added and the layers are separated. The water layer is extracted with $CH_2Cl_2$ and the organic layers are combined. The organic layer is washed with brine, dried ($Na_2SO_4$) and concentrated. The residue is distilled under vacuum (10 mm Hg) to provide. the silyl ether E1b.

b. Methyl 7-(5-but-3-enyl-2-hydroxy-4-(1,1,2,2-tetramethyl-1-silapropoxy)cyclopentyl) heptanoate (E1c): To a slurry of Mg° powder (2 equiv.) in THF at room temperature is added one crystal of iodine (catalytic $I_2$) and 1-bromobutene (2 equiv.) dropwise over 10 minutes. The reaction proceeds to exotherm as the addition continues. After the addition is complete, the reaction is refluxed for 3 hours and cooled to room temperature. The Grignard is diluted with THF and added via cannula to a 3-necked flask equipped with mechanical stirring and charged with CuBr.DMS (2 equiv.) in a 1:1 solution of THF/DMS at −78° C. After the addition of the Grignard (~20 minutes), the reaction is stirred for 1 hour at −78° C. The color of the reaction is dark red at this point. A solution of the ketone E1b (1 equiv.) in THF is then added dropwise over 25 minutes. The reaction is stirred at −78° C. for 15 minutes, then allowed to warm slowly to room temperature over 2 hours. The reaction is quenched with aqueous $NH_4Cl$ and the excess DMS is allowed to evaporate overnight. The reaction is partitioned between brine/ $CH_2Cl_2$ and the layers are separated. The aqueous layer is back-extracted with $CH_2Cl_2$ and the organic layers are combined and dried ($Na_2SO_4$). The solvent is removed in vacuo and the residue is chromatographed on $SiO_2$ (10% hexane/EtOAc) to give the ketone precursor to E1c.

The ketone precursor to E1c (1 equiv.) is dissolved in MeOH and cooled to −40° C. Sodium borohydride (0.9 equiv.) is added portionwise over 10 minutes. After the addition is complete, the reaction is stirred for 13 hours at −40° C. and then for 12 hours at −78° C. The reaction is quenched with water, partitioned between brine and $CH_2Cl_2$, and the layers separated. The aqueous layer is back-extracted with $CH_2Cl_2$ and the organic layers are combined and dried ($Na_2SO_4$). The solvent is removed in vacuo and the residue chromatographed on $SiO_2$ (30% EtOAc/hexanes) to give the alcohol E1c.

c. Methyl 7-(5-but-3-enyl-2,4-di(1,1,2,2-tetramethyl-1-silapropoxy) cyclopentyl) heptanoate (E1d): The alcohol E1c (1 equiv.) is dissolved in $CH_2Cl_2$ and cooled to 0° C. and 2,6 lutidine (1.3 equiv.) is added dropwise over 15 minutes. The solution is kept at −78° C., and TBDMS Triflate (1.2 equiv.) in $CH_2Cl_2$ is added dropwise over 15 minutes. The reaction is warmed gradually to room temperature and stirred at room temperature for 15 hours. Aqueous 10% HCl is added and the layers are separated. The water layer is extracted with $CH_2Cl_2$ and the organic layers are combined. The organic layer is washed with brine, dried ($Na_2SO_4$) and concentrated. The residue is chromatographed (10% EtOAc in hexanes) to provide the silyl ether E1d.

d. Methyl 7-(5-(3-oxopropanyl)-2,4-di(1,1,2,2-tetramethyl-1-silapropoxy) cyclopentyl) heptanoate (E1e): In a 50 mL round-bottomed flask, sodium periodate (2 equiv.) and 10 mL of water are added. This is stirred until the periodate has completely dissolved. Then an equal portion of glacial acetic acid is added, followed by two portions of tetrahydrofuran. Finally, a few mole percent of potassium osmate are added, followed by the alkene E1d (1 equiv.). The reaction is stirred at room temperature under nitrogen with TLC being used to monitor the reaction. When no starting material is evident by TLC, The reaction is quenched with brine and is extracted with ethyl acetate and hexanes in a 4:1 ratio. The organic layer is washed with brine to neutral pH, dried over sodium sulfate, and concentrated. After column chromatography, (7:3, Hexane: Ethyl Acetate) E1e is obtained.

e. 9,11-(1,1,2,24tetramethyl-1-silapropoxy)-13,14-dihydro-16-17-didehyro-17-(o-fluoro-phenyl) prostaglandin $F_{1\alpha}$ E1f): In a Round bottom flask is added chromium(II) chloride (2eq) and Nickel (II) chloride (0.02 eq). DMF is added and the solution is stirred. To this is added alpha bromo-(o-fluro)styrene (2eq) and the aldehyde (1eq). The reaction is monitored by TLC and then quenched with ammonium chloride when starting material is no longer present. The mixture is extracted into ethyl ether and washed with brine to neutral pH, dried with Magnesium sulfate, and concentrated. After column chromatography, (7:3, hexane: ethyl acetate) E1f is obtained.

f. 13,14-dihydro-16-17-Z-didehyro-17-(2-fluorophenyl) prostaglandin $F_{1\alpha}$ (E1g): To a small round-bottomed flask, is added methyl ester E1f and 3 mL of $CH_3CN$. Then 0.1 mL of HF/Pyridine (0.1 mmol, 1 equiv.) are added while the flask is warmed from 0° C. to room temperature. After 3 hours at 21° C., the reaction is quenched with saturated aqueous NaCl. The aqueous layer is extracted three times with $CH_2Cl_2$. The organic layers are combined and washed three times with 1N HCl, brine, and dried ($Na_2SO_4$). After column chromatography (7:3, Hexane: Ethyl Acetate), a clear oil is obtained. This oil is added to a few mL of a 3:1 THF: water solution, and the flask is cooled to 0° C. An excess amount (2.5 equiv.) of lithium hydroxide is added, the ice bath is removed, and the reaction is stirred at room temperature overnight. Methylene chloride and saturated citric acid are added to the reaction mixture, the aqueous layer is washed 3 times with methylene chloride, the organic. layers are combined and washed with brine, dried ($Na_2SO_4$), concentrated in vacuo, and the residue is chromatographed (methylene chloride, methanol, acetic acid, 9.6, 0.4, 0.015), to provide E1g.

Examples 2–17

Examples 2–17 are prepared. using substantially the same procedures as those described in Example 1, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 2

13,14-Dihydro-16-17-E-didehyro-17-(2-fluoro-phenyl)-17-trinor Prostaglandin $F_{1\alpha}$

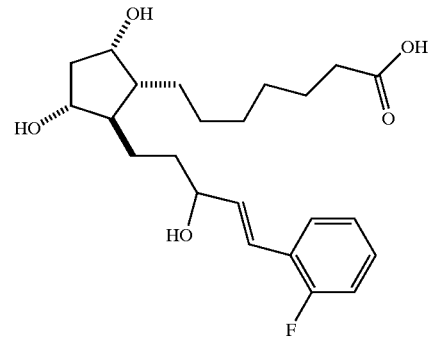

Example 3

13,14-Dihydro-E-16-17-didehyro-17-phenyl-17-trinor Prostaglandin $F_{1\alpha}$

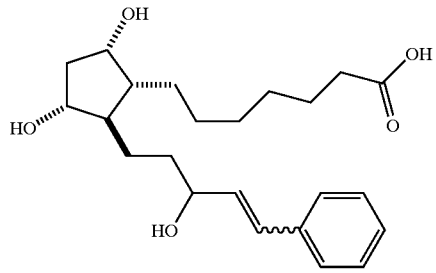

Example 4

13,14-Dihydro-E-16-17-didehyro-17-(2,4-dichloro-phenyl)-17-trinor Prostaglandin $F_{1\alpha}$

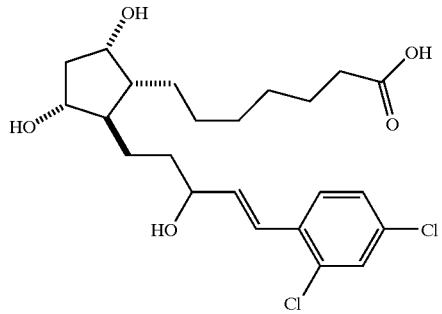

Example 5

13,14-Dihydro-E-16-17-didehyro-17-(2-fluoro-4-methylphenyl)-17-trinor Prostaglandin $F_{1\alpha}$

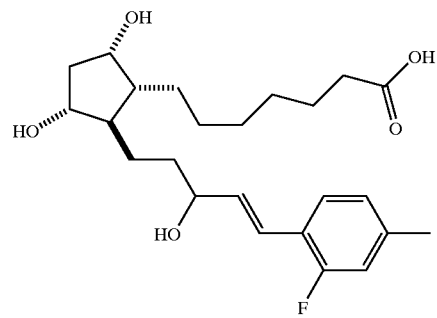

Example 6

13,14-Dihydro-E-16-17-didehyro-17-(2-fluoro-5-chloro-phenyl)-17-trinor Prostaglandin $F_{1\alpha}$

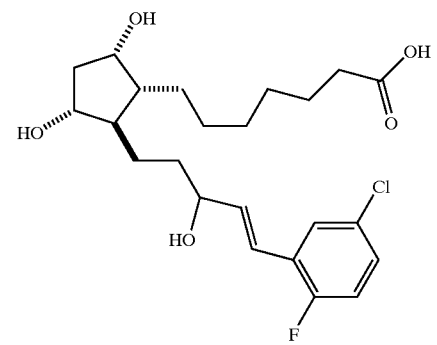

Example 7

13,14-Dihydro-E-16-17-didehyro-17-(2,5-difluoro-phenyl)-17-trinor Prostaglandin $F_{1\alpha}$

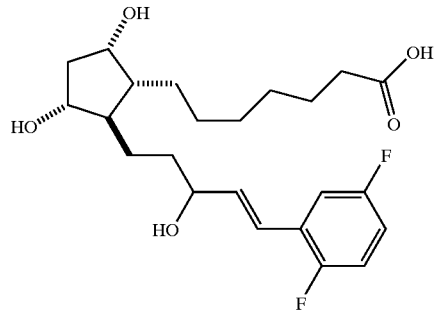

Example 8

13,14-Dihydro-E-16-17-didehyro-17-(2-fluoro-3-chloro-phenyl)-17-trinor Prostaglandin $F_{1\alpha}$

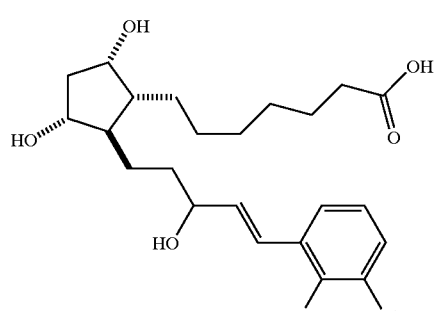

Example 9

13,14-Dihydro-E-16-17-didehyro-17-(2-fluoro-3-methoxy-phenyl)-17-trinor Prostaglandin $F_{1\alpha}$

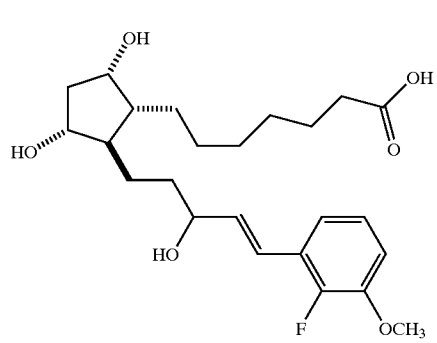

Example 10

13,14-Dihydro-16-17-didehyro-17-(3-fluoro-phenyl)-17-trinor Prostaglandin $F_{1\alpha}$

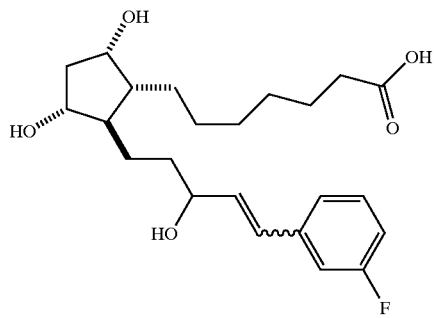

Example 11

13,14-Dihydro-16-17-didehyro-17-(4-fluoro-phenyl)-17-trinor Prostaglandin $F_{1\alpha}$

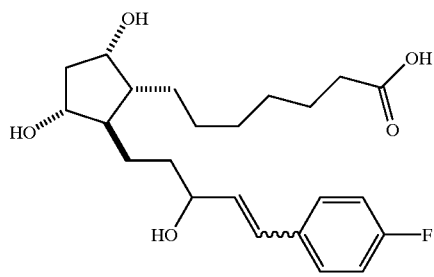

Example 12

13,14-Dihydro-E-16-17-didehyro-17-(3-trifluoromethyl-phenyl)-17-trinor Prostaglandin $F_{1\alpha}$

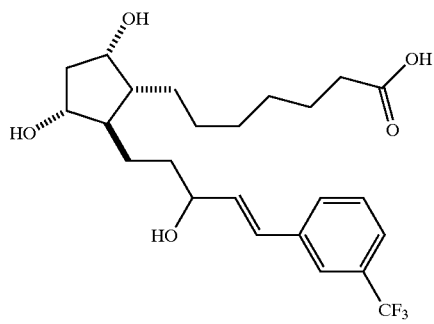

Example 13

13,14-Dihydro-16-17-dienyl-18-(phenyl)-18-dinor Prostaglandin $F_{1\alpha}$

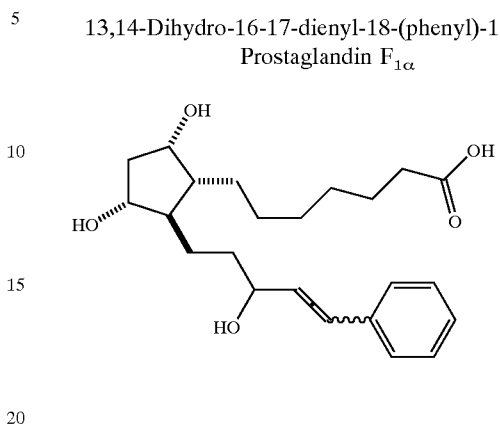

Example 14

13,14-Dihydro-16-17-dienyl-18-(2-fluoro-phenyl)-18-dinor Prostaglandin $F_{1\alpha}$

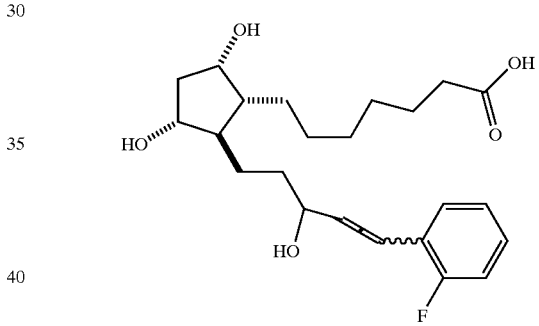

Example 15

13,14-Dihydro-16-17-dienyl-18-(2,4-difluoro-phenyl)-18-dinor Prostaglandin $F_{1\alpha}$

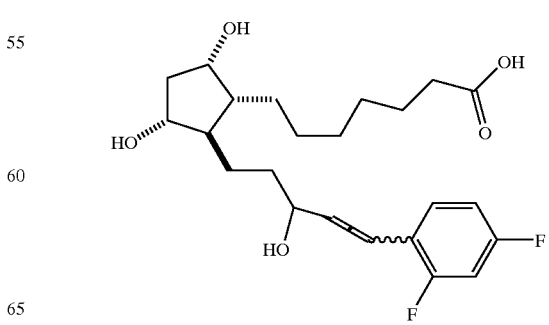

Example 16

13,14-Dihydro-16-17-dienyl-18-(3-trifluoromethyl-phenyl)-18-dinor Prostaglandin $F_{1\alpha}$

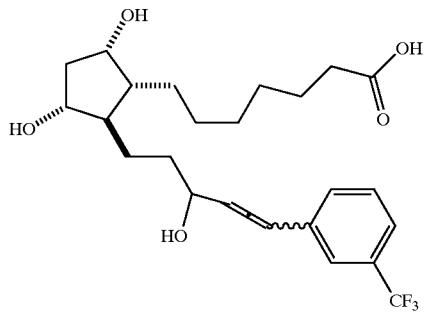

Example 17

13,14-Dihydro-16-17-dienyl-18-(4-methoxy-phenyl)-18-dinor Prostaglandin $F_{1\alpha}$

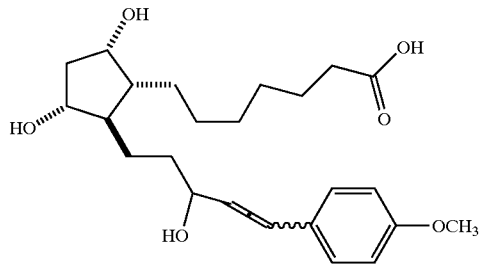

Example 18

Preparation of 13,14-Dihydro-16,17-alkenyl-17-(2-fluorophenyl)-17-trinor Prostaglandin F1α 1-Hydroxamic Acid

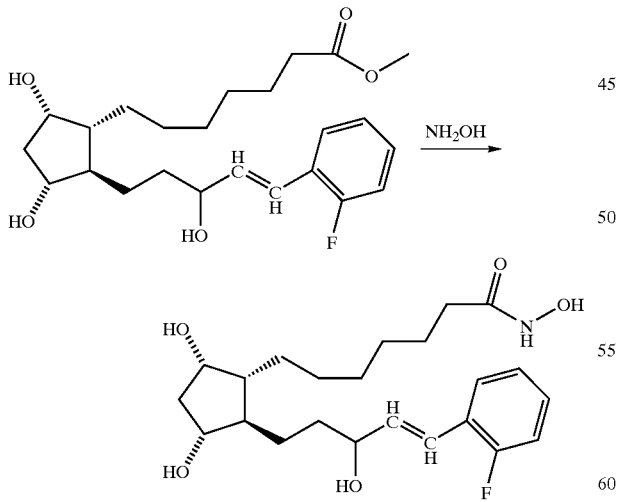

In a flame-dried round-bottomed flask equipped with a magnetic stir bar is placed 13,14-dihydro-16,17-alkenyl-17-(2-fluorophenyl) trinor Prostaglandin $F_{1\alpha}$ methyl ester (Example 1) (1.0 equiv.) in methanol. To this solution is added hydroxylamine in methanol (1.25 equiv.). The solution stirred for a few minutes. The solution is then treated with 1N hydrochloric acid and extracted with ethyl acetate. The organic layer is washed with brine, dried over anhydrous $MgSO_4$, filtered and concentrated under reduced pressure. The residue is purified by chromatography to give 13,14-dihydro-16,17-alkenyl-17-(2-fluorophenyl) trinor Prostaglandin $F_{1\alpha}$ 1-hydroxamic acid.

Examples 19–20

Examples 19–20 are prepared using substantially the same procedures as those described in Example 18, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 19

13,14-Dihydro-15,16-dienyl-17-phenyl-17-trinor Prostaglandin $F_1\alpha$ 1-Hydroxamic Acid

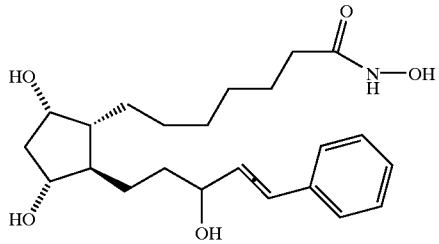

Example 20

13,14-Dihydro-16,17-alkenyl-17-(3-fluorophenyl)-17-trinor Prostaglandin $F_{1\alpha}$ 1-N-Methanesulfonamide

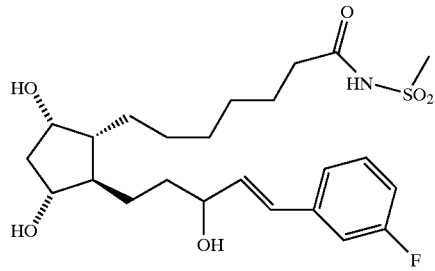

Example 21

13,14-Dihydro-16-keto-17-phenyl-17-trinor Prostaglandin $F_1\alpha$

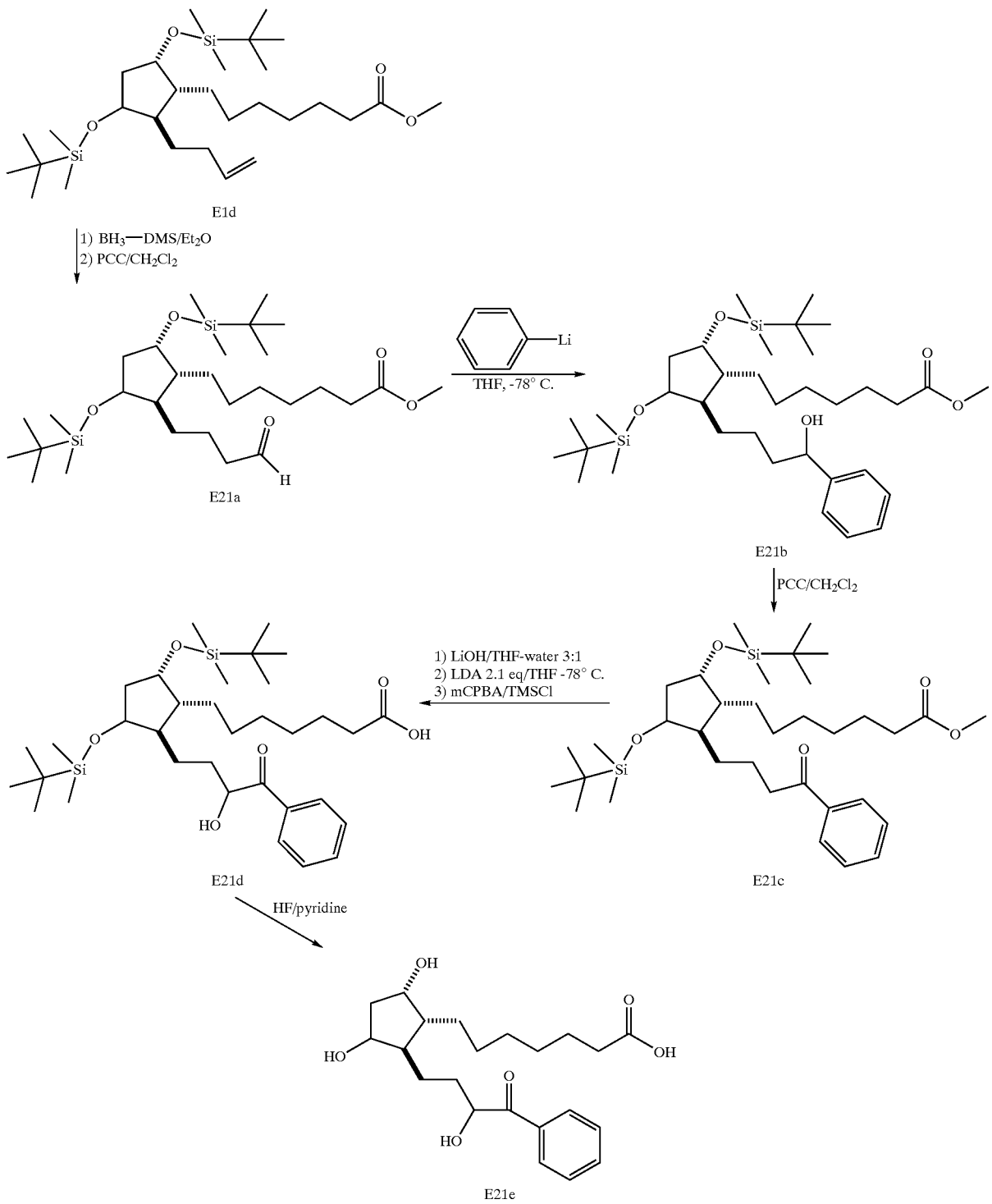

a. Methyl 7-(5-(4-oxobutyl)-2,4-di(1,1,2,2-tetramethyl-1-silapropoxy) cyclopentyl) heptanoate (E21a): In a 50 mL round-bottomed flask, Borane-dimethyl sulfide adduct (2 equiv.) and 10 mL of ethyl ether are added. This is stirred until the borane reagent has completely dissolved. The flask is cooled to 0° C. and the alkene is added in portions. When the reaction is complete by TLC, the mixture is poured into a well-stirred solution of pyridinium chlorochromate (PCC) in dichloromethane. The reaction is stirred at room temperature under nitrogen with TLC monitoring of the reaction. When no starting material is evident by TLC, the reaction is quenched with a saturated ammonium chloride solution and is extracted with ethyl acetate and hexanes in a 4:1 ratio. The organic layer is washed with brine to neutral pH, dried over sodium sulfate, and concentrated. After column chromatography, (1:1.5, Hexane: Ethyl Acetate) E21a is obtained.

b. Methyl 7-(5-(4-hydroxy-4-phenylbutyl)-2,4-di(1,1,2,2-tetramethyl-1-silapropoxy) cyclopentyl) heptanoate (E21b): To a 50 mL round bottom flask is added phenyl lithium (1 eqiv.) in THF and it is cooled to −78° C. To this flask is then added E21a in THF and is stirred for 30 minutes. The reaction was monitored by TLC and then quenched with ammonium chloride when starting material was no longer present. The mixture is extracted into ethyl ether and washed with brine to neutral pH, dried over magnesium sulfate, and concentrated. After column chromatography, (7:3, hexane: ethyl acetate) E21b is obtained.

c. Methyl 7-(5-(4-oxo-4-phenylbutyl)-2,4-di(1,1,2,2-tetramethyl-1-silapropoxy) cyclo pentyl) heptanoate (E21c): To a small round-bottomed flask is added methyl ester E21b and a portion of dichloromethane. Added slowly is PCC and activated sieves. The solution is stirred at room temperature and monitored by TLC until further oxidation ceases. At this point, the crude material is filtered through Fluorosil, concentrated and chromatographed to separate the ketone from the residual alcohol. After column chromatography, (7:3, hexane: ethyl acetate) E21c is obtained.

d. 7-(5-(3-hydroxy-4-oxo-4-phenylbutyl)-2,4-di(1,1,2,2-tetramethyl-1-silapropoxy) cyclo pentyl) heptanoic acid (E21d): The oil E21c is added to a few mL of a 3:1 THF water solution, and the flask is cooled to 0° C. An excess amount (2.5 equiv.) of lithium hydroxide is added, the ice bath is removed, and the reaction is stirred at room temperature overnight. Methylene chloride and saturated citric acid are added to the reaction mixture, the aqueous layer is washed 3, times with methylene chloride, the organic layers are combined and washed with brine, dried ($Na_2SO_4$), concentrated in vacuo, and the residue is chromatographed (methylene chloride, methanol, acetic acid, 9.6, 0.4, 0.015), to provide the free acid which is then dissolved in THF and cooled to −78° C. A THF solution containing 2.1 equivalents of LDA is added, followed by 2.2 equivalents of TMSCl. This is followed by 1.1 equivalents of mCPBA and the entire reaction is allowed to warm to room temperature. An acidic workup ensues, followed by extraction into a 3:1 mixture of ethyl acetate/hexane, yielding the hydroxy ketone E21d.

e. 13,14-dihydro-16-keto-17-phenyl-17-trinor Prostaglandin $F_{1\alpha}$ (E21e): To a small round-bottomed flask, are added acid E21d and a portion of $CH_3CN$ and HF/Pyridine (0.1 mmol, 1 equiv.) while the flask is slowly warmed from 0° C. to room temperature. After 3 hours at 21 ° C., the reaction is quenched with saturated aqueous NaCl. The aqueous layer is extracted three times with $CH_2Cl_2$. The organic layers are combined and washed three times with 0.1N HCl, brine, and dried ($Na_2SO_4$), and the residue is chromatographed (methylene chloride, methanol, acetic acid, 9.6, 0.4, 0.015), to provide the final product.

Examples 22–27

Examples 22–27 are prepared using substantially the same procedures as those described in Example 21, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 22

13,14-Dihydro-16-keto-16-(3,5-difluorophenyl)-16-tetranor Prostaglandin $F_{1\alpha}$

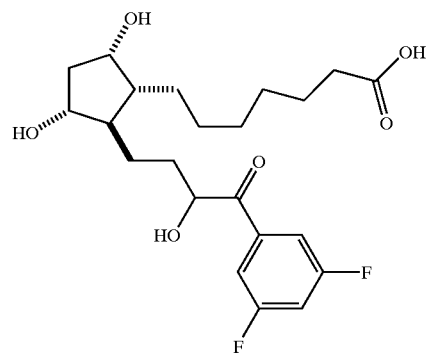

Example 23

13,14-Dihydro-16-oxo-16-(2-furanyl)-16-tetranor Prostaglandin $F_{1\alpha}$

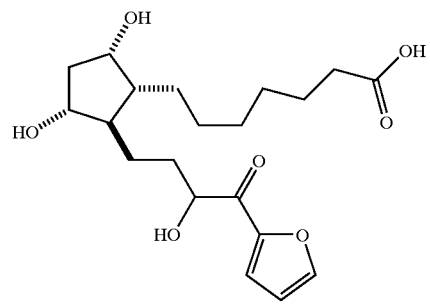

Example 24

13,14-Dihydro-16-oxo, 16-(3-Chloro-5-methylphenyl)-16-tetranor Prostaglandin $F_{1\alpha}$

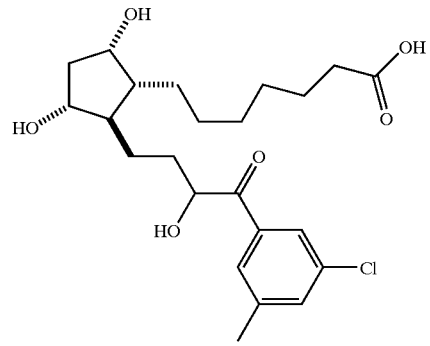

Example 25

13,14-Dihydro-16-keto-16-(4-fluorobenzo[b]furan-2-yl)-16-tetranor Prostaglandin F$_{1\alpha}$

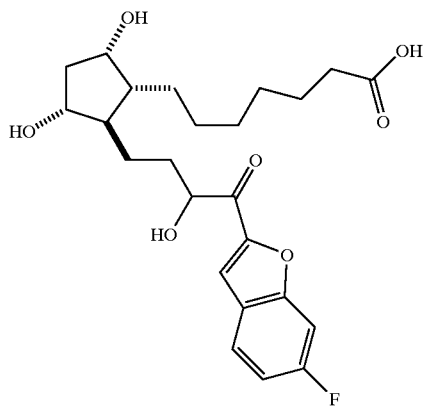

Example 26

13,14-Dihydro-16-oxo-16-(2-thianaphthyl)-16-tetranor Prostaglandin F$_{1\alpha}$

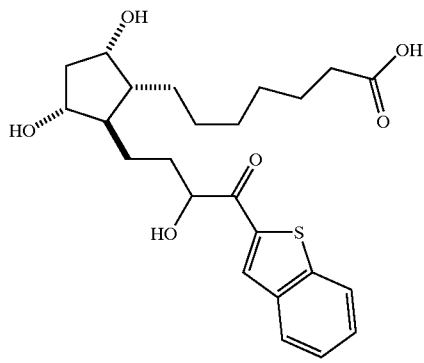

Example 27

13,14-Dihydro-16-oxo-17-(2-benzothiazolyl)-16-tetranor Prostaglandin F$_{1\alpha}$

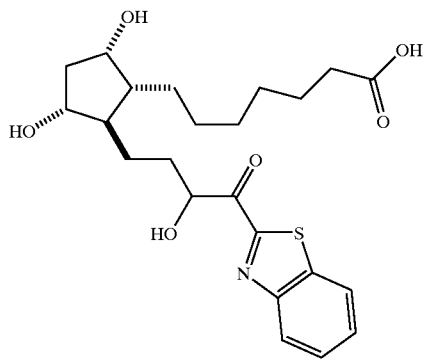

Example 28

Preparation of 13,14-Dihydro-16-oxo-16-(2,4-difluorophenyl)-16-tetranor PGF1α 1-Hydroxamic Acid

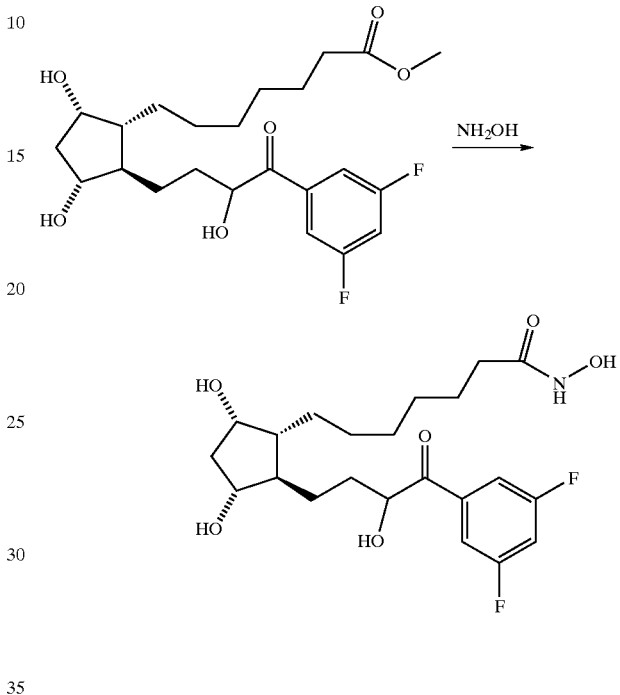

In a flame-dried 25 mL round-bottomed flask equipped with a magnetic stir bar is 13,14-dihydr-16,17-alkenyl-17-o-fluorophenyl trinor PGF$_{1\alpha}$ methyl ester (Example 22) (1.0 equiv.) in methanol. To this solution is added hydroxylamine in methanol (1.25 equiv.). The solution stirred for a few minutes. The solution is then treated with 1.0 N hydrochloric acid (HCl) and extracted twice with portions of ethyl acetate. The organic layer is washed with brine, dried over anhydrous MgSO$_4$, filtered and concentrated under reduced pressure. The residue is purified by chromatography to is 13,14-dihydro-16,17-alkenyl-17-(2-fluorophenyl) trinor PGF$_{1\alpha}$ 1-hydroxamic acid.

Examples 29–30

Examples 29–30 are prepared using substantially the same procedures as those described in Example 28, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 29
13,14-Dihydro-16-oxo-16-(4-methylphenyl)-16-tetranor Prostaglandin $F_1\alpha$ 1-Hydroxamic Acid
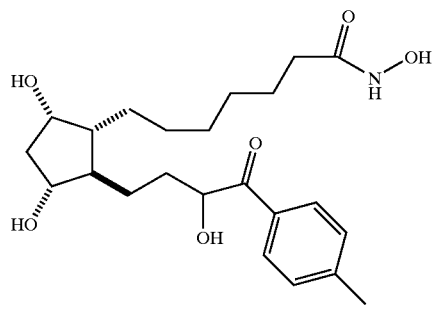
Example 30
13,14-Dihydro-16-oxo,16-(2-thianaphthyl)-16-tetranor Prostaglandin $F_1\alpha$ 1-N-Methanesulfonamide
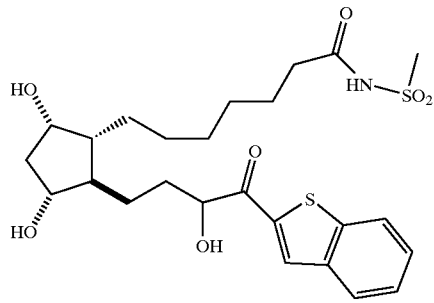
Example 31
13,14-Dihydro-15-(N-phenylcarbamoyl)-15-pentanor Prostaglandin $F_1\alpha$
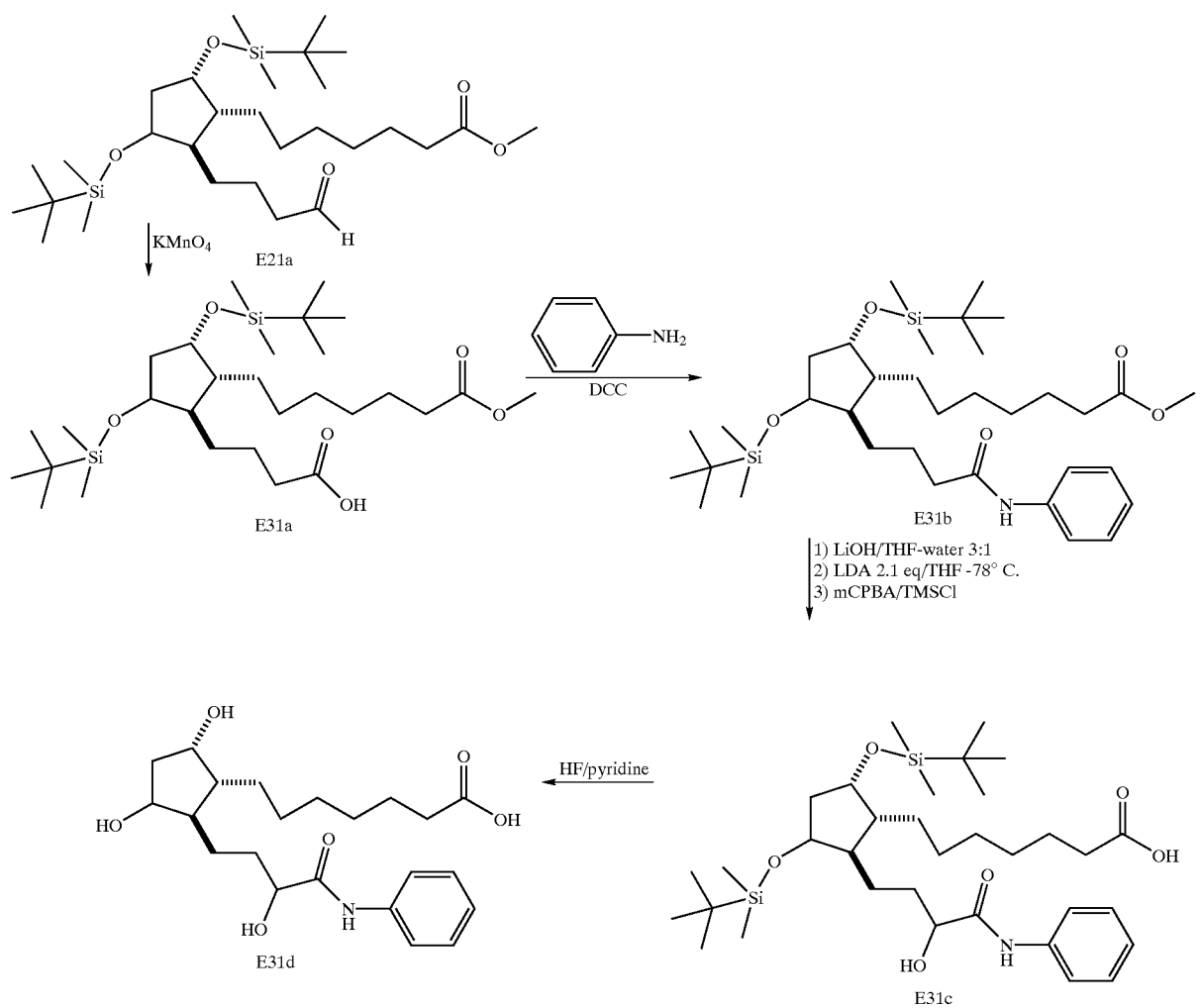

a. Methyl 7-(5-(4-carboxybutyl)-2,4-di(1,1,2,2-tetramethyl-1-silapropoxy) cyclopentyl) heptanoate (E31a): In a 50 mL round-bottomed flask, compound E21a is added. There follows a titration with a neutral solution of potassium permanganate (KMnO$_4$). When the reaction is complete by TLC, the mixture is washed with saturated sodium citrate and extracted three times with dichloromethane. The organic layer is separated, dried over sodium sulfate, and concentrated. After column chromatography, (methylene chloride, methanol, acetic acid, 9.6, 0.4,:0.015), E31a is obtained.

b. Methyl 7-(5-(3-N-phenylcarbamyl-propyl)-2,4di(1,1,2,2-tetramethyl-1-silapropoxy) cyclopentyl) heptanoate (E31b): To a 50 mL round bottom flask is added aniline (1 equiv.) in THF, then dicyclohexylcarbodiimide (DCC) is added in excess. To this flask is then added E31a in THF and is stirred for 30 minutes. The reaction is monitored by TLC and slight heat is applied if necessary, then quenched with ammonium chloride when starting material is no longer present. The mixture is extracted into ethyl ether and washed with brine to neutral pH, dried over magnesium sulfate, and concentrated. After column chromatography, (1:1, hexane: ethyl acetate) E31b is obtained.

d. 7-(5-(3-hydroxy4-oxo4-phenylbutyl)-2,4-di(1,1,2,2-tetramethyl-1-silapropoxy) cyclo pentyl) heptanoic acid (E31c): E31b is added to a few mL of a 3:1 THF: water solution, and the flask is cooled to 0° C. An excess amount (2.5 equiv.) of lithium hydroxide is added, the ice bath is removed, and the reaction is stirred at room temperature overnight. Methylene chloride and saturated citric acid are added to the reaction mixture, the aqueous layer is washed three times with methylene chloride, the organic layers are combined and washed with brine, dried (Na$_2$SO$_4$), concentrated in vacuo, and the residue is chromatographed (methylene chloride, methanol, acetic acid, 9.6, 0.4, 0.015), to provide the free acid which is then dissolved in THF and cooled to −78° C. A THF solution containing 2.1 equivalents of LDA is added, followed by 2.2 equivalents of TMSCl. This is followed by 1.1 equivalents of mCPBA and the entire reaction is allowed to warm to room temperature. An acidic workup ensues, followed by extraction into a 3:1 mixture of ethyl acetate/hexane, yielding the hydroxy amide E31c.

e. 13,14-dihydro-15-(N-phenylcarbamoyl)-15-pentanor Prostaglandin F$_1$α (E31d):

To a small round-bottomed flask, are added acid E31c and a portion of CH$_3$CN and HF/Pyridine (0.1 mmol, 1 equiv.) while the flask is slowly warmed from 0° C. to room temperature. After 3 hours at 21° C., the reaction is quenched with saturated aqueous NaCl. The aqueous layer is extracted three times with CH$_2$Cl$_2$. The organic layers are combined and washed three times with 0.1N HCl, brine, and dried (Na$_2$SO$_4$), and the residue is chromatographed (methylene chloride, methanol, acetic acid, 9.6, 0.4, 0.015), to provide the final product.

Examples 32–37

Examples 32.37 are prepared using substantially the same procedures as those described in Example 31, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 32

13,14-Dihydro-15-(N-3,4-difluorophenyicarbamoyl)-15-pentanor Prostaglandin F$_{1\alpha}$

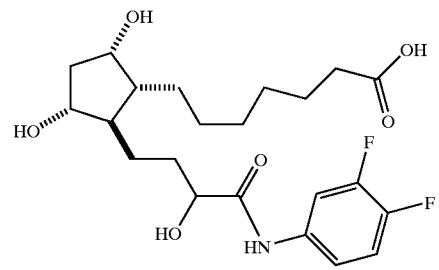

Example 33

13,14-Dihydro-15-(N-2-furanylcarbamoyl)-15-pentanor Prostaglandin F$_{1\alpha}$

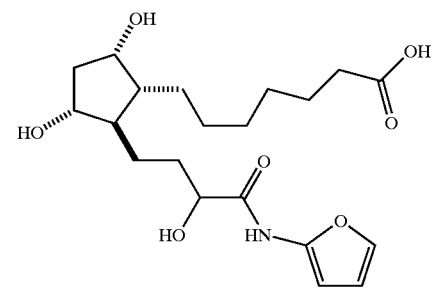

Example 34

13,14-Dihydro-15-(N-2-fluorophenylcarbamoyl)-15-pentanor Prostaglandin F$_{1\alpha}$

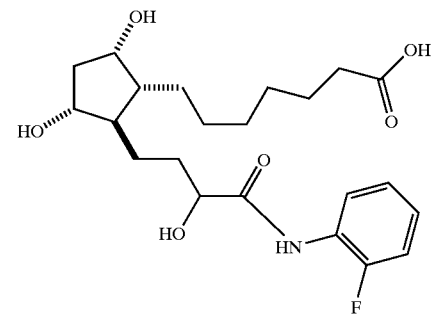

Example 35

13,14-Dihydro-15-(phenoxycarbonyl)-15-pentanor Prostaglandin $F_{1\alpha}$

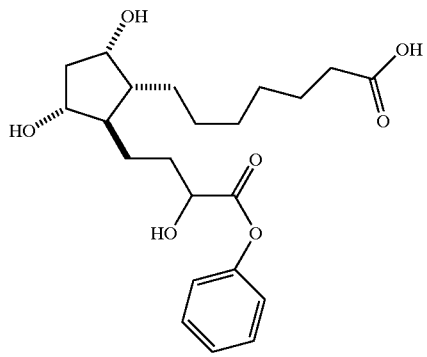

Example 36

13,14-Dihydro-15-(2-fluorophenoxycarbonyl)-15-pentanor Prostaglandin $F_{1\alpha}$

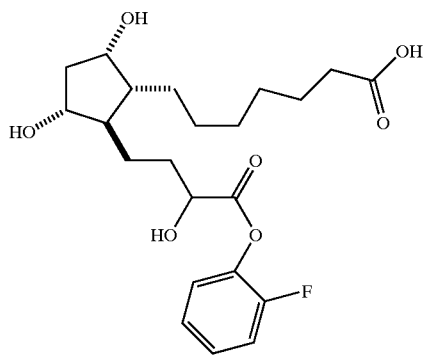

Example 37

13,14-Dihydro-15-(3-trifluoromethylthiaphenoxycarbonyl)-15-pentanor Prostaglandin $F_{1\alpha}$

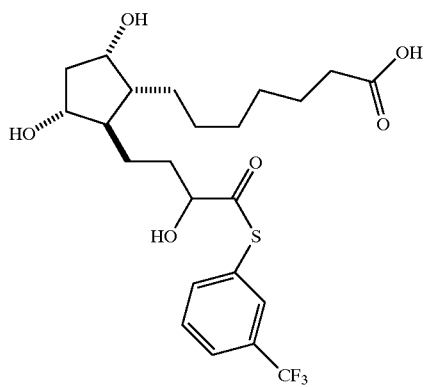

Examples 38–40

Examples 38–40 are prepared using substantially the same procedures as those described in Example 28, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 38

Preparation of 13,14-Dihydro-15-(N-3,4-difluorophenylcarbamoyl)-15-pentanor $PGF_{1\alpha}$ 1-Hydroxamic Acid

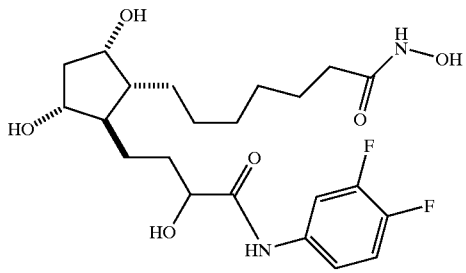

Example 39

Preparation of 13,14-dihydro-15-(N-3-chlorophenylcarbamoyl)-15-pentanor $PGF_{1\alpha}$ 1-Hydroxamic Acid

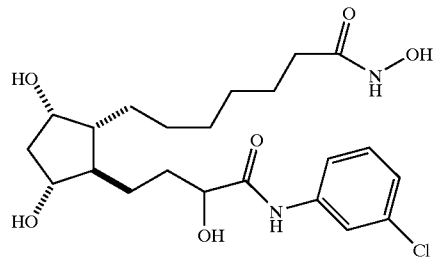

Example 40

Preparation of 13,14-Dihydro-15-(N-phenylcarbamoyl)-15-pentanor $PGF_{1\alpha}$ 1-N Methane Sulfonamide

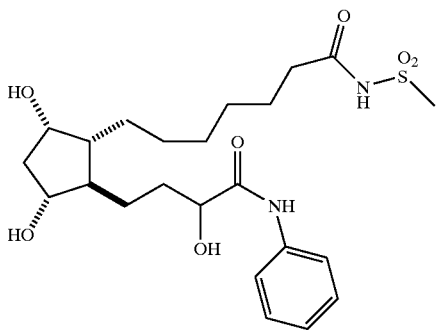

Example 41

Preparation of 13,14-Dihydro-17-aza-16-enyl-17-phenyl-17-trinor PGF$_{1\alpha}$

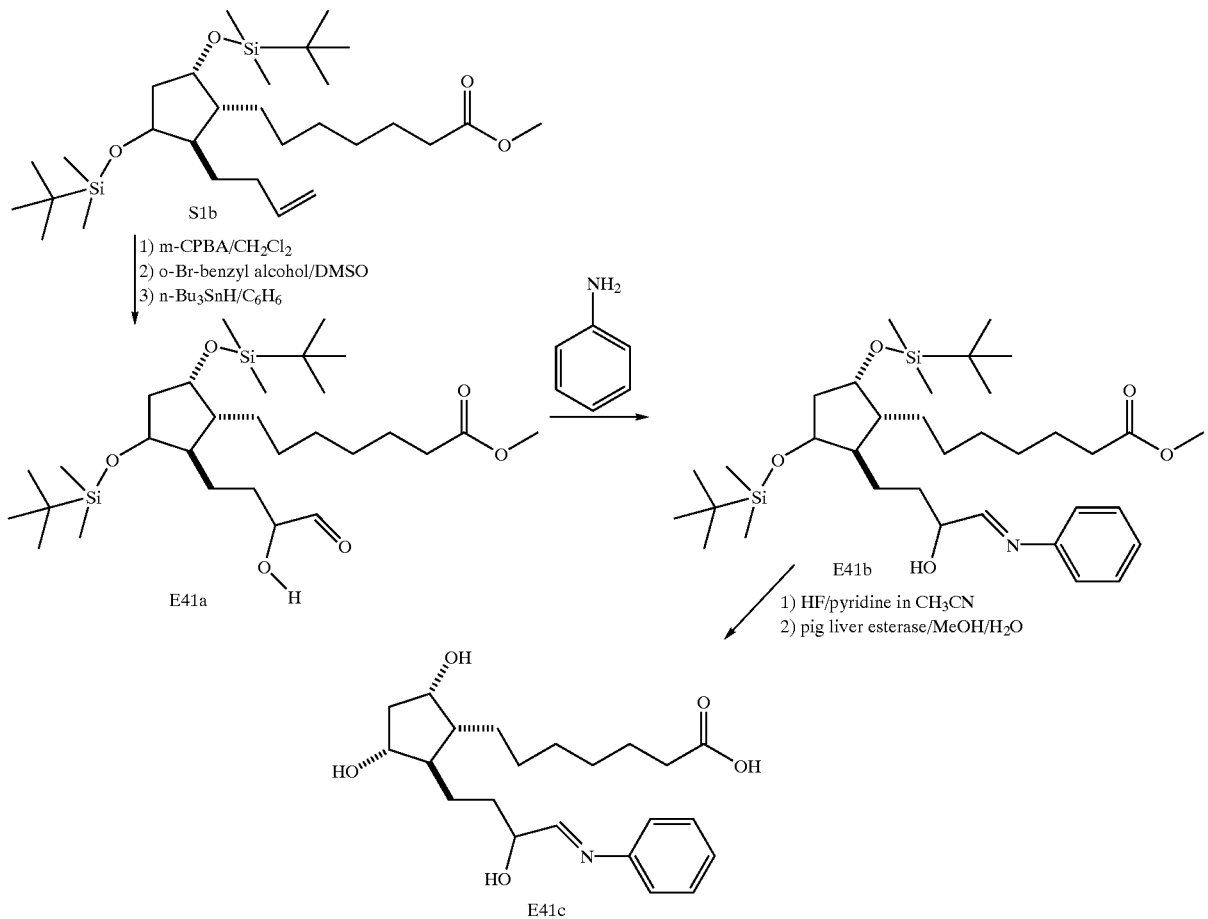

a. Methyl 7-(5-(3-hydroxy-4-oxobutylbutyl)-2,4-di(1,1,2,2-tetramethyl-1-silapropoxy) cyclopentyl) heptanoate (E41a): In a 50 mL round-bottomed flask, compound E21a is added, followed by a portion of methylene chloride (CH$_2$Cl$_2$). There follows addition of a slight molar excess of meta-chloroperoxybenzoic acid (m-CPBA) (Aldrich). When the reaction is complete by TLC, the mixture is washed with sodium sulfite solution, the organic layer is separated, is dried over sodium sulfate, and is concentrated. After column chromatography (20% EtOAc in hexanes), the epoxide as a clear oil is obtained. This oil is dissolved in DMSO and an equivalent of o-bromo-benzyl alcohol is added. This is heated to effect the nucleophilic opening of the epoxide by the alcohol. The material is added to a portion of brine and extracted exhaustively with a 3:1 mixture of ethyl acetate and hexanes. This material is chromatographed (10% EtOAc in hexanes) to provide the benzyl ether as an oil. The benzyl ether is then dissolved in benzene and a dilute solution of tri-n-butyl tin hydride is slowly added at the temperature increased to reflux. More hydride is added if needed to ensure complete reaction. The aldehyde thus recovered, E41a, is carefully chromatographed on silica gel (20% EtOAc in hexanes).

b. Methyl 7-(5-(5-aza-3-hydroxypent-4-enyl)-2,4-di(1,1,2,2-tetramethyl-1-silapropoxy) cyclopentyl) heptanoate (E41b): To a 50 mL round bottom flask is added aniline (1 equiv.) in C$_6$H$_6$, then E41a. The mixture is then heated and the water formed is removed by azetropic distillation with a Dean-Stark trap. The reaction is monitored by TLC. The product is isolated by removal of the benzene in vacuo, and column chromatography, (1:1, hexane: ethyl acetate) yields E41b.

c. 13,14-dihydro-17-aza-16-enyl-17-phenyl-17-trinor PGF$_{1\alpha}$(E41c): To a small round-bottomed flask, is added methyl ester E41b and a portion CH$_3$CN and HF/Pyridine (0.1 mmol, 1 equiv.) while the flask is slowly warmed from 0° C. to room temperature. After 3 hours at 21° C., the reaction mixture is added to a silica gel chromatography column and chromatographed with 5% methanol in CH$_2$Cl$_2$ to yield the dihydroxy ester. This ester is saponified by adding it dropwise in methanol to a gently stirred aqueous solution of pig liver esterase (Sigma) buffered at pH=7. Care must be taken to ensure that the total concentration of the MeOH remains below 10% (v/v). When the reaction is complete by TLC, the solution is acidified with citric acid, and is extracted three times with CH$_2$Cl$_2$. The organic layers are combined and washed with brine, and dried (Na$_2$SO$_4$), and the residue is chromatographed (methylene chloride, methanol, acetic acid, 9.6, 0.4, 0.015), to provide the final product.

Examples 42–45

Examples 42–45 are prepared using substantially the same procedures as those described in Example 41, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 42

13,14-Dihydro-17-aza-16-enyl-17-(2-fluorophenyl)-17-trinor PGF$_{1\alpha}$

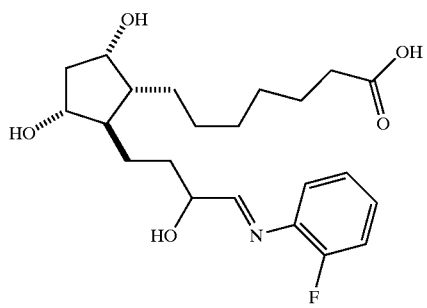

Example 43

13,14-Dihydro-17-aza-16-enyl-17-(-2-furanyl)-17-trinor Prostaglandin F$_{1\alpha}$

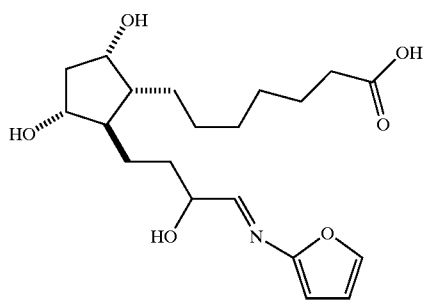

Example 44

13,14-Dihydro-17-aza-16-enyl-17-(4-phenylphenyl)-17-trinor Prostaglandin F$_{1\alpha}$

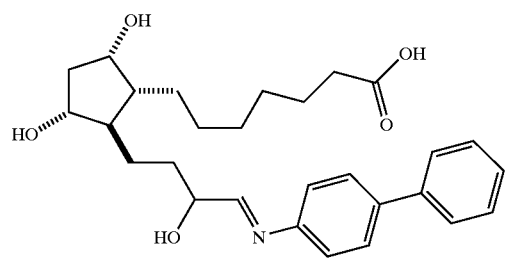

Example 45

13,14-Dihydro-17-aza-16-enyl-17-(3-fluorophenyl)-17-trinor Prostaglandin F$_{1\alpha}$

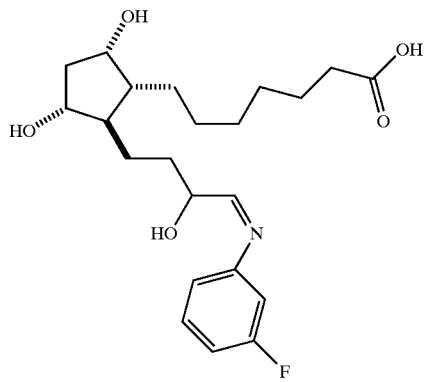

Examples 46–48

Examples 46–48 are prepared using substantially the same procedures as those described in Example 28, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 46

Preparation of 13,14-Dihydro-17-aza-16-enyl-17-(-2-furanyl)-17-trinor Prostaglandin F$_{1\alpha}$ 1-Hydroxamic Acid

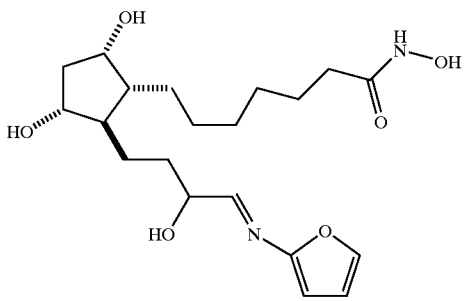

Example 47

Preparation of 13,14-Dihydro-17-aza-16-enyl-17-(3-chlorophenyl)-17-trinor Prostaglandin $F_{1\alpha}$ 1-Hydroxamic Acid

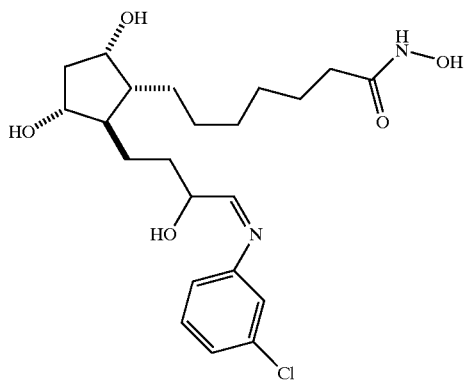

Example 48

Preparation of 13,14-Dihydro-17-aza-16enyl-17-(-2-thiofuranyl)-17-trinor Prostaglandin $F_{1\alpha}$ 1-N-Methanesulfonamide

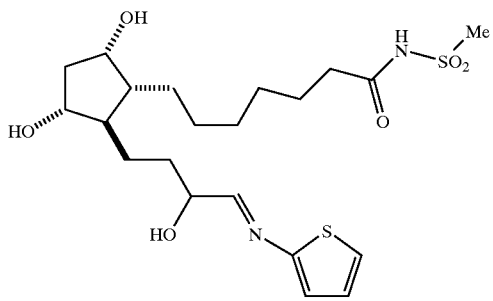

Compositions

Compositions of the subject invention comprise a safe and effective amount of the subject compounds, and a pharmaceutically-acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of the treatment, the nature of concurrent therapy, the particular pharmaceutically-acceptable carrier utilized, and like factors within the knowledge and expertise of the attending physician.

In addition to the compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a subject. The term "compatible", as used herein, means that the components of the composition are capable of being commingled with the compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the subject being treated.

Some examples of substances which can serve as pharmaceutically-acceptable carriers or components thereof are sugars, such as lactose, glucose and sucrose; starches, such as cornstarch and potato starch; cellulose and its derivatives, such as sodium carboxymethyl cellulose, ethyl cellulose, cellulose acetate; powdered tragacanth; malt; gelatin; talc; solid lubricants, such as stearic acid, magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; alginic acid; emulsifiers, such as the Tweens®; wetting agents such as sodium lauryl sulfate; coloring agents; flavoring agents, excipients; tableting agents; stabilizers; antioxidants; preservatives; pyrogen-free water; isotonic saline; and phosphate buffer solutions.

The choice of a pharmaceutically-acceptable carrier to be used in conjunction with a compound is basically determined by the way the compound is to be administered. The compounds of the present invention may be administered systemically. Routes of administration include transdermal; oral; parenterally, including subcutaneous or intravenous injection; topical; and/or intranasal.

The appropriate amount of the compound to be used may be determined by routine experimentation with animal models. Such models include, but are not limited to the intact and ovariectomized rat models, the ferret, canine, and non human primate models as well as disuse models.

Preferred unit dosage forms for injection include sterile solutions of water, physiological saline, or mixtures thereof. The pH of said solutions should be adjusted to about 7.4. Suitable carriers for injection or surgical implants include hydrogels, controlled- or sustained release devises, polylactic acid, and collagen matrices.

Suitable pharmaceutically-acceptable carriers for topical application include those suited for use in lotions, creams, gels and the like. If the compound is to be administered perorally, the preferred unit dosage form is tablets, capsules and the like. The pharmaceutically-acceptable carriers suitable for the preparation of unit dosage forms for oral administration are well-known in the art. Their selection will depend on secondary considerations like taste, cost, and shelf stability, which are not critical for the purposes of the subject invention, and can be made without difficulty by those skilled in the art.

Methods of Use

The compounds of the present invention are useful in treating many medical disorders, including for example, ocular disorders, hypertension, fertility control, nasal congestion, neurogenic bladder disorder, gastrointestinal disorders, dermatological disorders, and osteoporosis.

The compounds of the present invention are useful in increasing bone volume and trabecular number through formation of new trabeculae, bone mass while maintaining a normalized bone turnover rate, and formation at the endosteal surface without removing bone from the existing cortex. Thus, these compounds are useful in the treatment and prevention of bone disorders.

The preferred routes of administration for treating bone disorders are transdermal and intranasal. Other preferred routes of administration include rectal, sublingual, and oral.

The dosage range of the compound for systemic administration is from about 0.01 to about 1000 µg/kg body weight, preferably from about 0.1 to about 100 µg/kg per body weight, most preferably form about 1 to about 50 µg/kg body weight per day. The transdermal dosages will be designed to attain similar serum or plasma levels, based upon techniques known to those skilled in the art of pharmacokinetics and transdermal formulations. Plasma levels for systemic administration are expected to be in the range of 0.01 to 100 nanograms/ma, more preferably from 0.05 to 50 ng/ml, and most preferably from 0.1 to 10 ng/ml. While these dosages are based upon a daily administration rate, weekly or monthly accumulated dosages may also be used to calculate the clinical requirements.

Dosages may be varied based on the patient being treated, the condition being treated, the severity of the condition being treated, the route of administration, etc. to achieve the desired effect.

The compounds of the present invention are also useful in decreasing intraocular pressure. Thus, these compounds are useful in the treatment of glaucoma. The preferred route of administration for treating glaucoma is topically.

Composition and Method Examples

The following non-limiting examples illustrate the subject invention. The following composition and method examples do not limit the invention, but provide guidance to the skilled artisan to prepare and use the compounds, compositions and methods of the invention. In each case other compounds within the invention may be substituted for the example compound shown below with similar results. The skilled practitioner will appreciate that the examples provide guidance and may be varied based on the condition being treated and the patient.

Example A

Pharmaceutical compositions in the form of tablets are prepared by conventional methods, such as mixing and direct compaction, formulated as follows:

| Ingredient | Quantity (mg per tablet) |
| --- | --- |
| Compound of Example 1 | 5 |
| Microcrystalline Cellulose | 100 |
| Sodium Starch Glycollate | 30 |
| Magnesium Stearate | 3 |

When administered orally once daily, the above composition substantially increases bone volume in a patient suffering from osteoporosis.

Example B

Pharmaceutical compositions in liquid form are prepared by conventional methods, formulated as follows:

| Ingredient | Quantity |
| --- | --- |
| Compound of Example 32 | 1 mg |
| Phosphate buffered physiological saline | 10 ml |
| Methyl Paraben | 0.05 ml |

When 1.0 ml of the above composition is administered subcutaneously once daily, the above composition substantially increases bone volume in a patient suffering from osteoporosis.

Example C

Topical pharmaceutical compositions for lowering intraocular pressure are prepared by conventional methods and formulated as follows:

| Ingredient | Amount (wt %) |
| --- | --- |
| Compound of Example 1 | 0.004 |
| Dextran 70 | 0.1 |
| Hydroxypropyl methylcellulose | 0.3 |
| Sodium Chloride | 0.77 |
| Potassium chloride | 0.12 |
| Disodium EDTA (Edetate disodium) | 0.05 |
| Benzalkonium chloride | 0.01 |
| HCL and/or NaOH | pH 7.2–7.5 |
| Purified water | q.s. to 100% |

While particular embodiments of the subject invention have been described, it would be obvious to those skilled in the art that various changes and modifications to the compositions disclosed herein can be made without departing from the spirit and scope of the invention. It is intended to cover, in the appended claims, all such modifications that are within the scope of this invention.

What is claimed is:

1. A compound having the structure:

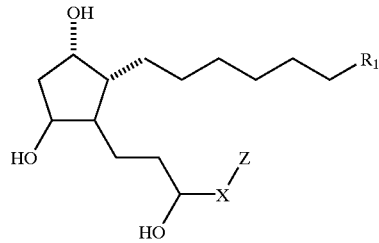

wherein
(a) $R_1$ is selected from the group consisting of $CO_2H$, $C(O)NHOH$, $CO_2R_2$, $CH_2OH$, $S(O)_2R_2$, $C(O)NHR_2$, $C(O)NHS(O)_2R_2$, or tetrazole; wherein $R_2$ is alkyl, heteroalkyl, carbocyclic aliphatic ring, heterocyclic aliphatic ring, monocyclic aromatic ring, or monocyclic heteroaromatic ring;
(b) X is selected from the group consisting of $CH=C=CH$, $CH=CH$, $CH=N$, $C(O)$ and $C(O)Y$; wherein Y is selected from the group consisting of O, S and NH;
(c) Z is an aromatic ring or a heteroaromatic ring provided that when Z is a heteroaromatic ring Z is attached via a Carbon member atom; and
(d) any optical isomer, diastereomer, entinaomer of the above structure or a pharmaceutically-acceptable salt, or bio-hydrolyzable amide, ester, or imide thereof.

2. The compound of claim 1 wherein $R_1$ is selected from the group consisting of $CO_2H$, $C(O)NHOH$, $CO_2R_2$, $C(O)NHS(O)_2R_2$, or tetrazole.

3. The compound of claim 2, wherein X is CH—C=CH or C(O)Y.

4. The compound of claim 3, wherein Z is monocyclic.

5. The compound of claim 4, wherein Z is selected from the group consisting of: phenly, thienyl, and furanyl.

6. The compound of claim 5, wherein Z substituted with one substitute, said one substitutent being selected from the group consisting of: lower alkyl, halo, and haloalkyl.

7. The compound of claim 6, wherein $R_1$ is $CO_2H$ or $CO_2R_2$.

8. The compound of claim 7, wherein $R_2$ is selected from the group consisting of methyl, ethyl and isopropyl.

9. The compound of claim 2, wherein X is CH=CH, CH=N, or C(O).

10. The compound of claim 9, wherein Z is bicyclic.

11. The compound of claim 10, wherein Z is a bicyclic heteroaromatic ring.

12. The compound of claim 11, wherein Z is selected from the group consisting of benzo[β]thiazolyl, benzo[β]thiophenyl and benzoxazoyl.

13. The compound of claim 12, wherein Z is substituted with one subtituent, wherein the substituent is selected from the group consisting of lower alkyl, halo and haloalkyl.

14. The compound of claim 13, wherein $R_1$ is $C(O)_2H$ or $CO_2R_2$.

15. The compound of claim 14, wherein $R_2$ is selected from the group consisting methyl, ethyl and isopropyl.

16. A method of treating or preventing a bone disorder in human or other animal subject in need of such treatment by administering to said human other animal subject a compound having the structure:

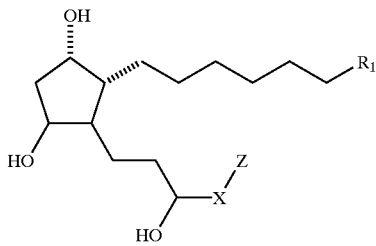

wherein
(a) $R_1$ is selected from the group consisting of $CO_2H$, C(O)NHOH, $CO_2R_2$, $CH_2OH$, $S(O)_2R_2$, $C(O)NHR_2$, $C(O)NHS(O)_2R_2$, or tetrazole; wherein $R_2$ is alkyl, heteroalkyl, carbocyclic aliphatic ring, heterocyclic aliphatic ring, monocyclic aromatic ring, or monocyclic heteroaromatic ring;
(b) X is selected from the group consisting of CH=C=CH, CH=CH, CH=N, C(O) and C(O)Y, wherein Y is selected from the group consisting of O, S and NH;
(c) Z is an aromatic ring or a heteroaromatic ring provided that when Z is a heteroaromatic ring Z is attached via a Carbon member atom; and
(d) any optical isomer, diastereomer, enantiomer of the above structure or a pharmaceutically-acceptable salt, or bio-hydrolyzable amide, ester, or imide thereof.

17. The method of claim 16, wherein the bone disorder is selected from the group consisting of osteoporosis, osteopenia and bone fracture.

18. The method of claim 17, wherein the compound is administered transdermally.

19. A method of treating glaucoma, said method comprising administering to a human or other animal a safe and effective amount of a compound according to the structure:

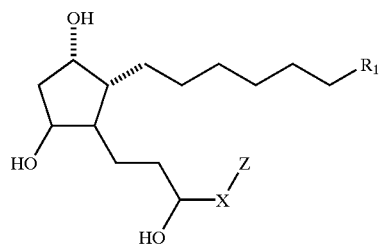

wherein
(a) $R_1$ is selected from the group consisting of $CO_2H$, C(O)NHOH, $CO_2R_2$, $CH_2OH$, $S(O)_2R_2$, $C(O)NHR_2$, $C(O)NHS(O)_2R_2$, or tetrazole; wherein $R_2$ is alkyl, heteroalkyl, carbocyclic aliphatic ring, heterocyclic aliphatic ring, monocyclic aromatic ring, or monocyclic heteroaromatic ring;
(b) X is selected from the group consisting of CH=C=CH, CH=CH, CH=N, C(O) and C(O)Y; wherein Y is selected from the group consisting of O, S and NH;
(c) Z is an aromatic ring or a heteroaromatic ring provided that when Z is a heteroaromatic ring Z is attached via a Carbon member atom; and
(d) any optical isomer, diastereomer, enantiomer of the above structure or a pharmaceutically acceptable salt, or bio-hydrolyzable amide, ester, or imide thereof.

20. The method of claim 19, wherein the compound is administered topically.

* * * * *

UNITED STATES PATENT AND TRADEMARK OFFICE
CERTIFICATE OF CORRECTION

PATENT NO. : 6,451,859 B1  Page 1 of 1
DATED : September 17, 2002
INVENTOR(S) : Mitchell Anthony deLong et al.

It is certified that error appears in the above-identified patent and that said Letters Patent is hereby corrected as shown below:

Column 6,
Line 34, delete "Ill" and insert -- III --.

Column 11,
Line 61, delete "isolaited" and insert -- isolated --.

Column 17,
Line 45, delete "24tetrmethyl" and insert -- 2-tetramethyl --.

Column 33,
Line 24, delete "oxo4" and insert -- oxo-4 --.

Signed and Sealed this

Thirtieth Day of September, 2003

JAMES E. ROGAN
*Director of the United States Patent and Trademark Office*